US012642770B2

(12) United States Patent
Klein et al.

(10) Patent No.: US 12,642,770 B2
(45) Date of Patent: Jun. 2, 2026

(54) LIPOSOMIC DRUG-DELIVERY VEHICLES

(71) Applicant: Yeda Research and Development Co. Ltd., Rehovot (IL)

(72) Inventors: Jacob Klein, Rehovot (IL); Ronit Goldberg, Rehovot (IL); Weifeng Lin, Rehovot (IL)

(73) Assignee: Yeda Research and Development Co. Ltd., Rehovot (IL)

( * ) Notice: Subject to any disclaimer, the term of this patent is extended or adjusted under 35 U.S.C. 154(b) by 315 days.

(21) Appl. No.: 18/202,981

(22) Filed: May 29, 2023

(65) Prior Publication Data

US 2023/0301915 A1 Sep. 28, 2023

Related U.S. Application Data

(63) Continuation of application No. 16/485,855, filed as application No. PCT/IL2018/050178 on Feb. 16, 2018, now Pat. No. 11,684,578.

(60) Provisional application No. 62/459,624, filed on Feb. 16, 2017.

(51) Int. Cl.
*A61K 9/1273* (2025.01)
*A61K 9/00* (2006.01)
*A61P 19/02* (2006.01)

(52) U.S. Cl.
CPC .......... *A61K 9/1273* (2013.01); *A61K 9/0019* (2013.01); *A61P 19/02* (2018.01)

(58) Field of Classification Search
CPC ...... A61K 9/1273; A61K 9/0019; A61P 19/02
See application file for complete search history.

(56) References Cited

U.S. PATENT DOCUMENTS

| | | | | |
|---|---|---|---|---|
| 8,617,592 | B2 | 12/2013 | Jiang et al. | |
| 10,730,976 | B2 | 8/2020 | Klein et al. | |
| 2002/0041861 | A1* | 4/2002 | Brey ......................... | C11C 3/00 530/395 |
| 2012/0114756 | A1 | 5/2012 | Emanuel et al. | |
| 2016/0015810 | A1 | 1/2016 | Deschatelets et al. | |
| 2019/0374466 | A1 | 12/2019 | Klein et al. | |
| 2020/0332033 | A1 | 10/2020 | Klein et al. | |
| 2020/0364807 | A1 | 11/2020 | Thoele et al. | |

FOREIGN PATENT DOCUMENTS

| | | |
|---|---|---|
| CN | 1294625 | 5/2001 |
| CN | 101265304 | 9/2008 |
| CN | 105126179 | 12/2015 |
| EP | 0251229 | 1/1988 |
| IL | 234929 | 12/2014 |
| JP | 06-178930 | 6/1994 |
| JP | 2002-500165 | 1/2002 |
| JP | 03-308010 | 7/2002 |
| JP | 2004-535434 | 11/2004 |
| JP | 05-412078 | 2/2014 |
| WO | WO 99/33940 | 7/1999 |
| WO | WO 2010/067617 | 6/2010 |
| WO | WO 2015/001564 | 1/2015 |
| WO | WO 2015/193887 | 12/2015 |
| WO | WO 2015/193888 | 12/2015 |
| WO | WO 2016/051413 | 4/2016 |
| WO | WO 2017/109784 | 6/2017 |
| WO | WO 2018/150429 | 8/2018 |
| WO | WO 2018/150429 A9 | 8/2018 |

OTHER PUBLICATIONS

Parenteral drug delivery; https://clinicalgate.com/parenteral-drug-delivery (site accessed Jul. 2025) (Year: 2015).*
Advisory Action Dated Jan. 12, 2023 from the US Patent and Trademark Office Re. U.S. Appl. No. 16/485,855. (5 pages).
Communication Pursuant to Article 94(3) EPC Dated Aug. 5, 2022 From the European Patent Office Re. Application No. 18708225.0. (6 Pages).
Decision on Rejection Dated Mar. 28, 2023 From the State Intellectual Property Office of the People's Republic of China Re. Application No. 201880025272.3. (4 pages).
English Translation Dated Feb. 21, 2022 of Notification of Office Action and Search Report Dated Jan. 27, 2022 From the State Intellectual Property Office of the People's Republic of China Re. Application No. 201880025272.3. (7 Pages).
Final Official Action Dated Aug. 26, 2021 from the US Patent and Trademark Office Re. U.S. Appl. No. 16/485,855. (14 pages).
International Preliminary Report on Patentability Dated Aug. 29, 2019 From the International Bureau of WIPO Re. Application No. PCT/IL2018/050178. (8 Pages).
International Search Report and the Written Opinion Dated Jun. 4, 2018 From the International Searching Authority Re. Application No. PCT/IL2018/050178. (26 Pages).
Interview Summary Dated Jan. 24, 2023 from the US Patent and Trademark Office Re. U.S. Appl. No. 16/485,855. (2 pages).
Notice of Allowance Dated Feb. 15, 2023 From the US Patent and Trademark Office Re. U.S. Appl. No. 16/485,855. (4 Pages).
Notice of Reason(s) for Rejection Dated Nov. 24, 2021 From the Japan Patent Office Re. Application No. 2019-543877. (3 Pages).
Notification of Office Action and Search Report Dated Jan. 27, 2022 From the National Intellectual Property Administration of the People's Republic of China Re. Application No. 201880025272.3 Together With English Claims. (11 Pages).

(Continued)

*Primary Examiner* — Robert A Wax
*Assistant Examiner* — John W Lippert, III

(57) ABSTRACT

A liposome for use in delivering a therapeutically active agent to a subject in need thereof is disclosed herein. The liposome comprises:

a) at least one bilayer-forming lipid;

b) a polymeric compound having the general formula I:

Formula I

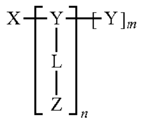

wherein m, n, L, X, Y, and Z are as defined herein; and c) a therapeutically active agent, incorporated in the liposome and/or on a surface of the liposome.

21 Claims, 6 Drawing Sheets

Specification includes a Sequence Listing.

(56) References Cited

OTHER PUBLICATIONS

Notification of Office Action and Search Report Dated Mar. 31, 2021 From the National Intellectual Property Administration of the People's Republic of China Re. Application No. 201880025272.3 and Its Translation Into English. (18 Pages).
Notification of Office Action Dated Aug. 17, 2022 From the National Intellectual Property Administration of the People's Republic of China Re.Application No. 201880025272.3 and Its Translation Into English. (14 Pages).
Office Action Dated Jul. 4, 2021 From the Israel Patent Office Re. Application No. 268714 and Its Translation Into English. (6 Pages).
Office Action Dated Sep. 14, 2022 From the Israel Patent Office Re. Application No. 291628. (5 Pages).
Official Action Dated Mar. 2, 2021 From the US Patent and Trademark Office Re. U.S. Appl. No. 16/485,855. (13 Pages).
Official Action Dated Mar. 18, 2022 from US Patent and Trademark Office Re. U.S. Appl. No. 16/485,855. (10 pages).
Official Action Dated Sep. 21, 2022 from US Patent and Trademark Office Re. U.S. Appl. No. 16/485,855. (10 pages).
Restriction Official Action Dated Oct. 30, 2020 From the US Patent and Trademark Office Re. U.S. Appl. No. 16/485,855. (6 Pages).
Translation Dated Dec. 10, 2021 of Notice of Reason(s) for Rejection Dated Nov. 24, 2021 From the Japan Patent Office Re. Application No. 2019-543877. (3 Pages).
Translation Dated Apr. 12, 2023 of Decision on Rejection Dated Mar. 28, 2023 From the State Intellectual Property Office of the People's Republic of China Re. Application No. 201880025272.3. (5 pages).
Adler et al. "Synthesis of Poly(2-Methacryloyloxyyethyl Phosphorylchlorine)-Conjugated Lipids and Their Characterization and Surface Properties of Modified Liposomes for Protein Interactions", Biomaterial Science, 9(17): 5854-5867, Published Online Jul. 20, 2021.
Bias et al. "Sustained-Release Dexamethasome Palmitate. Pharmacokinetics and Efficacy in Patients With Activated Inflammatory Osteoarthritis of the Knee", Clinical Drug Investigations, 21(6): 429-436, Jun. 2001.
Blume et al. "Liposomes for the Sustained Drug Release In Vivo", Biochimica et Biophysica Acta, 1029(1): 91-97, Nov. 2, 1990.
Bonanomi et al. "Studies of Pharmacokinetics and Therapeutic Effects of Glucocorticoids entrapped in Liposomes After Intraarticular application in Healthy Rabbits and in Rabbits With Antigen-Induced Arthritis", Rheumatology International, 7(5): 203-212, Sep. 1987.
Butoescu et al. "Intra-Articular Drug Delivery Systems for the Treatment of Rheumatic Diseases: A Review of the Factors Influencing Their Performance", European Journal of Pharmaceutics and Biopharmaceutics, 73(2): 205-218, Available Onlien Jun. 21, 2009.
Charrois et al. "Drug Release Rate Influences the Pharmacokinetics, Biodistribution, Therapeutic Activity, and Toxicity of Pegylated Liposomal Doxorubicin Formulations in Murine Breast Cancer", Biochimica et Biophysica Acta, 1663(1): 167-177, Available Online Apr. 12, 2004.
Chen et al. "Lubrication at Physiological Pressures by Polyzwitterionic Brushes", Science, 323(5922): 1698-1701, Mar. 27, 2009.
Evans et al. "Progress in Intra-Articular Therapy", Nature Reviews Rheumatology, 10(1): 11-22, Published Online Nov. 5, 2013.
Foong et al. "Treatment of Antigen-Induced Arthritis in Rabbits With Liposome-Entrapped Methotrexate Injected Intra-Articularly", The Journal of Pharmacy and Pharmacology, 45(3): 204-209, Mar. 1993.
Gabizon et al. "Prolonged Circulation Time and Enhanced Accumulation in Malignant Exudates of Doxorubicin Encapsulated in Polyethylene-Glycol Coated Liposomes", Cancer Research, 54(4): 987-992, Feb. 15, 1994.
Gerwin et al. "Intraarticular Drug Delivery in Osteoarthritis", Advanced Drug Delivery Reviews, 58(2): 226-242, Available Online Feb. 23, 2006.
Goldberg et al. "Boundary Lubricants With Exceptionally Low Friction Coefficients Based on 2D Close-Packed Phosphatidylcholine Liposomes", Advanced Materials, 23(31): 3517-3521, Published Online Jul. 4, 2011.
Goldberg et al. "Interactions Between Adsorbed Hydrogenated Soy Phosphatidylcholine (HSPC) Vesicles at Physiologically High Pressures and Salt Concentrations", Biophysical Journal, 100(10): 2403-2411, May 2011.
Goldberg et al. "Liposomes as Lubricants: Beyond Drug Delivery", Chemistry and Physics of Lipids, 165(4): 374-381, Available Online Nov. 19, 2011.
Harris et al. "Effect of Pegylation on Pharmaceuticals", Nature Reviews Drug Discovery, 2(3): 214-221, Mar. 2003.
Hunter et al. "The Individual and Socioeconomic Impact of Osteoarthritis", Nature Reviews Rheumatology, 10(7): 437-441, Published Online Mar. 25, 2014.
Hurley et al. "ESCAPE—Into the Community—A Community-Based Rehabilitation Programme for Elderly People With Chronic Joint Pain", Perspectives in Public Health, 136(2): 67-69, Mar. 2016.
Moghimi et al. "Stealth Liposomes and Long Circulating Nanoparticles: Critical Issues in Pharmacokinetics, Opsonization and Protein-Binding Properties", Progress in Lipid Research, 42(6): 463-478, Nov. 2003.
Seror et al. "Supramolecular Synergy in the Boundary Lubrication of Synovial Joints", Nature Communications, 6: 6497-1-6497-7, Mar. 10, 2015.
Sivan et al. "Liposomes Act as Effective Biolubricants for Friction Reduction in Human Synovial Joints", Langmuir, 26(2): 1107-1116, Published on Web Dec. 16, 2009.
Sorkin et al. "Origins of Extreme Boundary Lubrication by Phosphatidylcholine Liposomes", Biomaterials, 34(22): 5465-5475, Available Online Apr. 23, 2013.
Türker et al. "Enhanced Efficacy of Diclofenac Sodium-Loaded Lipogelosome Formualtion in Intra-Articular Treatment of Rheumatoid Arthritis", Journal of Drug Targeting, 16(1): 51-57, Jan. 2008.
Van den Hoven et al. "Liposomal Drug Formulations in the Treatment of Rheumatoid Arthritis", Molecular Pharmaceutics, XP055215890, 8(4): 1002-1015, Jun. 2, 2011.
Xu et al. "Novel Biomimetic Polymersomes as Polymer Therapeutics for Drug Delivery", Journal of Controlled Release, 107(3): 502-512, Available Online Sep. 9, 2005.
Requisition by the Examiner Dated Apr. 19, 2024 From the Innovation, Science and Economic Development Canada, Canadian Intellectual Property Office Re. Application No. 3,052,774. (4 Pages).
Communication Pursuant to Article 94(3) EPC Dated Nov. 17, 2025 From the European Patent Office Re. Application No. 18708225.0 (3 Pages).

* cited by examiner

LIPOSOMIC DRUG-DELIVERY VEHICLES

RELATED APPLICATIONS

This application is a continuation of U.S. patent application Ser. No. 16/485,855, filed on Aug. 14, 2019 which is a National Phase of PCT Patent Application No. PCT/IL2018/050178 having International Filing Date of Feb. 16, 2018, which claims the benefit of priority under 35 USC § 119(e) of U.S. Provisional Patent Application No. 62/459,624 filed on Feb. 16, 2017. The contents of the above applications are all incorporated by reference as if fully set forth herein in their entirety.

SEQUENCE LISTING STATEMENT

The XML file, entitled 96440SequenceListing.xml, created on May 29, 20203, comprising 3 KB, submitted concurrently with the filing of this application is incorporated herein by reference. The sequence listing submitted herewith is identical to the sequence listing forming part of the international application.

FIELD AND BACKGROUND OF THE INVENTION

The present invention, in some embodiments thereof, relates to therapy, and more particularly, but not exclusively, to novel polymeric compounds usable, inter alia, for forming drug delivery vehicles.

Liposomes have been extensively studied as drug carriers as they can incorporate essentially any kind of drug—including both hydrophilic and hydrophobic molecules. However, standard liposomes are rapidly removed from the blood, mainly by the cells of the mononuclear phagocyte system [Blume & Cevc, *Biochim Biophys Acta* 1990, 1029, 91-97].

The use of a phosphatidylethanolamine liposome with polyethylene glycol covalently attached to phosphatidylethanolamine (PE-PEG) has been reported to result in a long circulation time and high retention of the PEGylated liposomes compared with the pure (non-PEGylated) liposomes [Blume & Cevc, *Biochim Biophys Acta—Biomembranes* 1990, 1029, 91-97]. PEGylated liposomes are used in formulations of doxorubicin for treating cancer (e.g., Caelyx®, Doxil®) [Charrois & Allen, *Biochim Biophys Acta—Biomembranes* 2004, 1663, 167-177].

Osteoarthritis (OA) is a degenerative joint disease associated with progressive loss of articular cartilage, subchondral bone sclerosis, osteophyte formation, changes in synovial membrane and an increased volume of synovial fluid with reduced viscosity and lubrication properties [Gerwin et al., *Adv Drug Deliv Rev* 2006, 58:226-242]. OA is the most common type of arthritis imposing a huge burden [Hunter et al., *Nat Rev Rheumatol* 2014, 10:437-441] and affecting large numbers of people: for example, some 30 million in the US; 40 million in Europe; and eight and a half million in the United Kingdom, of whom six million are in constant pain [Hurley & Carter, *Perspect Public Health* 2016, 136:67-69].

Treatment of OA by local drug administration via intra-articular (IA) injection may reduce the systemic exposure to the drug and increase the efficiency of delivery in the targeted area while allowing increased levels of the therapeutic agents. Various glucocorticoid and hyaluronic acid (HA) formulations are available for IA treatment, providing at most only short-term short term pain relief. The half-life of drugs following IA injection has been reported to be several hours. This short half-life requires repeated injections, which results in poor patient compliance, and high risk of introduction of bacteria into the joint space [Butoescu et al., *Eur J Pharm Biopharm* 2009, 73:2015-218].

Treatment of antigen-induced arthritis in rabbits with liposome entrapped methotrexate administered by IA injection was reported to result in improved drug efficacy relative in comparison to the injection of the free drug. However, this enhanced effect was limited to suppression of arthritis after 7 days but not arthritis after 21 days [Foong & Green, *J Pharm Pharmacol* 1993, 45:204-209]. Loading of diclofenac sodium into a liposomal matrix for IA administration was reported to suppress joint swelling in antigen-induced arthritis [Turker et al., *J Drug Target* 2008, 16:51-57]. Dexamethasone palmitate encapsulated in lipid microspheres was reported to exhibit enhanced retention and a long-lasting therapeutic effect [Labrenz & Rose, *Clin Drug Invest* 2001, 21:429-436; Bonanomi et al., *Rheumatol Int* 1987, 7:203-212]. Liposomal dexamethasone palmitate, commercially available in Germany under the tradename Lipotalon® (Merckle), is the only liposomal formulation marketed for IA delivery, although several liposomal formulations for IA delivery have entered clinical trials [Evans et al., *Nat Rev Rheumatol* 2014, 10:11-22].

Intra-articular delivery of liposomal formulations suffer from irreproducibility associated with polydispersity and aggregation of liposomes consisting of multilamellar vesicle (MLV) vehicles, or from rapid clearance in the case of smaller unilamellar vesicles (SUVs) [Bonanomi et al., *Rheumatol Int* 1987, 7:203-212]. Liposome aggregates injected into the body are more prone to protein adsorption, and to attack and removal by macrophages [Moghimi & Szebeni, *Prog Lipid Res* 2003, 42:463-478].

Additional approaches for arthritis therapy include IA injection of viscous supplements of hyaluronic acid [Evans et al., *Nat Rev Rheumatol* 2014, 10:11-22] and the use of liposomes as bio-lubricants [Sivan et al., *Langmuir* 2010, 26:1107-1116].

U.S. Pat. No. 8,617,592 describes block copolymers and conjugates comprising a zwitterionic poly(carboxybetaine), poly(sulfobetaine) or poly(phosphobetaine) block, and a hydrophobic block, which self-assemble into particles, and the use of such particles for delivering therapeutic and diagnostic agents.

International Patent Application having publication No. WO 2017/109784 describes polymeric compounds comprising a lipid moiety and an ionic polymeric moiety, such as a pMPC (poly(O-(2-methacryloyloxyethyl)phosphorylcholine)) moiety, as well as bilayers and liposomes comprising such a polymeric compound in combination with a bilayer-forming lipid. The bilayers and/or liposomes comprising such polymeric compounds are described as being useful for reducing a friction coefficient of a surface and/or for inhibiting biofilm formation.

Additional background art includes Chen et al. [*Science* 2009, 323:1698-1702]; Gabizon et al. [*Cancer Res* 1994, 54:987-982]; Goldberg et al. [*Biophys J* 2011, 100:2403-2411]; Goldberg et al. [*Adv Materials* 2011, 23:3517-3521]; Goldberg & Klein [*Chem Phys Lipids* 2012, 165:374-381]; Harris & Chess [*Nat Rev Drug Discov* 2003, 2:214-221]; Seror et al. [*Nat Commun* 2015, 6:6497]; Sorkin et al. [*Biomaterials* 2014, 34:5465-5475]; International Patent Application Nos. PCT/IL2014/050604 (published as WO 2015/001564), PCT/IL2015/050605 (published as WO 2015/193887) and PCT/IL2015/050606 (published as WO 2015/193888); and Israel Patent Application No. 234929.

SUMMARY OF THE INVENTION

The present inventors have now surprisingly uncovered that recently designed lipid-derived polymeric compounds, in which monomers include both phosphate and ammonium ionic groups, can be efficiently used in delivering therapeutically active agents to a subject's bodily site.

Embodiments of the present invention relate to the use of such compounds in drug delivery (e.g., sustained release of drugs), and thereby in the treatment of medical conditions treatable by the drug.

According to an aspect of some embodiments of the invention, there is provided a liposome comprising:

a) at least one bilayer-forming lipid;

b) a polymeric compound having the general formula I:

Formula I

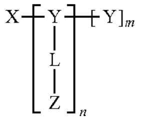

wherein:

m is zero or a positive integer;

n is an integer which is at least 1, wherein when X does not comprise a phosphate group, n is at least 2;

X is a lipid moiety;

Y is a backbone unit which forms a polymeric backbone;

L is absent or is a linking moiety; and

Z has the general formula II:

Formula II

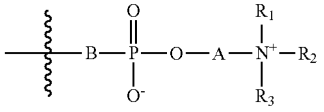

wherein:

A is a substituted or unsubstituted hydrocarbon;

B is an oxygen atom or is absent; and $R_1$-$R_3$ are each independently selected from the group consisting of hydrogen, alkyl, cycloalkyl, heteroalicyclic, aryl and heteroaryl; and c) a therapeutically active agent, incorporated in the liposome and/or on a surface of the liposome, the liposome being for use in delivering the therapeutically active agent to a subject in need thereof.

According to some embodiments of the invention, the liposome is for use in treating a medical condition treatable by the therapeutically active agent in the subject.

According to some embodiments of the invention, the delivering comprises sustained release of the therapeutically active agent.

According to some embodiments of the invention, the therapeutically effective agent is selected from the group consisting of an analgesic, an anti-inflammatory agent, an anti-proliferative agent, an anti-microbial agent, and a vaccine antigen.

According to some embodiments of the invention, the delivering is effected by parenteral systemic administration.

According to some embodiments of the invention, the delivering is effected by intra-articular administration.

According to some embodiments of the invention, the liposome is for use in the treatment of a synovial joint disorder.

According to some embodiments of the invention, the synovial joint disorder is selected from the group consisting of arthritis, bursitis, carpal tunnel syndrome, fibromyositis, gout, locked joint, tendinitis, traumatic joint injury, and joint injury associated with surgery.

According to some embodiments of the invention, the therapeutically active agent is an analgesic and/or anti-inflammatory agent.

According to some embodiments of the invention, a molar ratio of the bilayer-forming lipid and the polymeric compound is in a range of from 5:1 to 5,000:1.

According to some embodiments of the invention, Y is a substituted or unsubstituted alkylene unit.

According to some embodiments of the invention, Y is a substituted or unsubstituted ethylene unit.

According to some embodiments of the invention, Y has the formula $—CR_4R_5—CR_6D-$, wherein:

when Y is a backbone unit which is not attached to L or Z, D is $R_7$; and when Y is a backbone unit which is attached to L or Z, D is a covalent bond or a linking group attaching Y to L or Z, the linking group being selected from the group consisting of —O—, —S—, alkylene, arylene, sulfinyl, sulfonyl, phosphate, phosphonyl, phosphinyl, carbonyl, thiocarbonyl, urea, thiourea, O-carbamyl, N-carbamyl, O-thiocarbamyl, N-thiocarbamyl, C-amido, N-amido, C-carboxy, O-carboxy, sulfonamido, and amino; and $R_4$-$R_7$ are each independently selected from the group consisting of hydrogen, alkyl, alkenyl, alkynyl, cycloalkyl, aryl, heteroaryl, heteroalicyclic, halo, hydroxy, alkoxy, aryloxy, thiohydroxy, thioalkoxy, thioaryloxy, sulfinyl, sulfonyl, cyano, nitro, azide, azo, phosphate, phosphonyl, phosphinyl, oxo, carbonyl, thiocarbonyl, urea, thiourea, O-carbamyl, N-carbamyl, O-thiocarbamyl, N-thiocarbamyl, C-amido, N-amido, C-carboxy, O-carboxy, sulfonamido, and amino.

According to some embodiments of the invention, $R_4$ and $R_5$ are each hydrogen.

According to some embodiments of the invention, $R_6$ is hydrogen.

According to some embodiments of the invention, the linking group is selected from the group consisting of —O—, —C(═O)O—, —C(═O)NH— and phenylene.

According to some embodiments of the invention, the linking group is —C(═O)O—.

According to some embodiments of the invention, L is a substituted or unsubstituted hydrocarbon from 1 to 10 carbon atoms in length.

According to some embodiments of the invention, L is a substituted or unsubstituted ethylene group.

According to some embodiments of the invention, B is an oxygen atom.

According to some embodiments of the invention, A is a substituted or unsubstituted hydrocarbon from 1 to 4 carbon atoms in length.

According to some embodiments of the invention, A is a substituted or unsubstituted ethylene group.

According to some embodiments of the invention, $R_1$-$R_3$ are each independently hydrogen or $C_{1-4}$-alkyl.

According to some embodiments of the invention, $R_1$-$R_3$ are each methyl.

According to some embodiments of the invention, n is at least 3.

According to some embodiments of the invention, n is in a range of from 5 to 50, and m is in a range of from 0 to 50.

According to some embodiments of the invention, at least a portion of Y, L and/or Z comprises at least one targeting moiety.

According to some embodiments of the invention, the polymeric compound has the general formula Ib:

Formula Ib

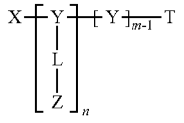

wherein:

- T is a unit of Y which comprises the at least one targeting moiety;
- X and T are attached to distal termini of the polymeric compound; and
- X, Y, L, Z, n and m are as defined for general formula I, with the proviso that m is a positive integer.

According to some embodiments of the invention, the lipid is selected from the group consisting of a fatty acid, a monoglyceride, a diglyceride, a triglyceride, a glycerophospholipid, a sphingolipid, and a sterol.

According to some embodiments of the invention, the glycerophospholipid is selected from the group consisting of a phosphatidyl ethanolamine, a phosphatidyl serine, a phosphatidyl glycerol and a phosphatidyl inositol.

According to some embodiments of the invention, X has the general formula III:

Formula III

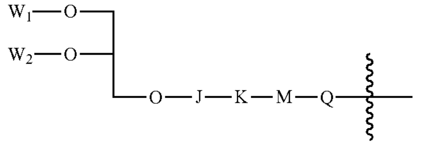

wherein:

- $W_1$ and $W_2$ are each independently selected from the group consisting of hydrogen, alkyl, alkenyl, alkynyl and acyl, wherein at least one of $W_1$ and $W_2$ is not hydrogen;
- J is —P(=O)(OH)—O— or absent;
- K is a substituted or unsubstituted hydrocarbon from 1 to 10 carbon atoms in length, or absent;
- M is a linking group selected from the group consisting of —O—, —S—, amino, sulfinyl, sulfonyl, phosphate, phosphonyl, phosphinyl, carbonyl, thiocarbonyl, urea, thiourea, carbamyl, thiocarbamyl, amido, carboxy, and sulfonamide, or absent; and
- Q is a substituted or unsubstituted hydrocarbon from 1 to 10 carbon atoms in length, wherein when M is absent, K is also absent.

According to some embodiments of the invention, J is —P(=O)(OH)—O— and K is selected from the group consisting of an ethanolamine moiety, a serine moiety, a glycerol moiety and an inositol moiety.

According to some embodiments of the invention, M is amido.

According to some embodiments of the invention, J and K are absent and M is carbonyl.

According to some embodiments of the invention, Q is dimethylmethylene ($—C(CH_3)_2—$).

According to some embodiments of the invention, at least one of $W_1$ and $W_2$ is alkyl, alkenyl, alkynyl or acyl, being from 10 to 30 carbon atoms in length.

According to some embodiments of the invention, the lipid moiety comprises at least one fatty acid moiety selected from the group consisting of lauroyl, myristoyl, palmitoyl, stearoyl, palmitoleoyl, oleoyl, and linoleoyl.

According to some embodiments of the invention, the liposome is formulated as part of a pharmaceutical composition, which further comprises a pharmaceutically acceptable carrier.

According to some embodiments of the invention, the carrier comprises an aqueous liquid.

According to some embodiments of the invention, the pharmaceutical composition further comprises a water-soluble biopolymer.

According to some embodiments of the invention, the biopolymer comprises hyaluronic acid.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE SEVERAL VIEWS OF THE DRAWINGS

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings:

FIG. 2A) or fluorescent-labeled hydrogenated soy phosphatidylcholine liposomes with 2 kDa pMPC moieties (Liposome-pMPC in FIG. 2A; HSPC-pMPC in FIG. 2B), with 2 kDa pMPC and trimethylammonium propane moieties (Liposome-pMPC/TAP in FIG. 2A; HSPC-TAP/pMPC in FIG. 2D) or 2 kDa PEG moieties (Liposome-PEG in FIG. 2A; HSPC-PEG in FIG. 2C); exponential fits and associated calculated half-lives (T½) of 95, 22 and 90 hours are presented in FIGS. 2B-2D, respectively; mean liposome diameter was 170 nm or 162 nm.

DESCRIPTION OF SPECIFIC EMBODIMENTS OF THE INVENTION

Figure 1:
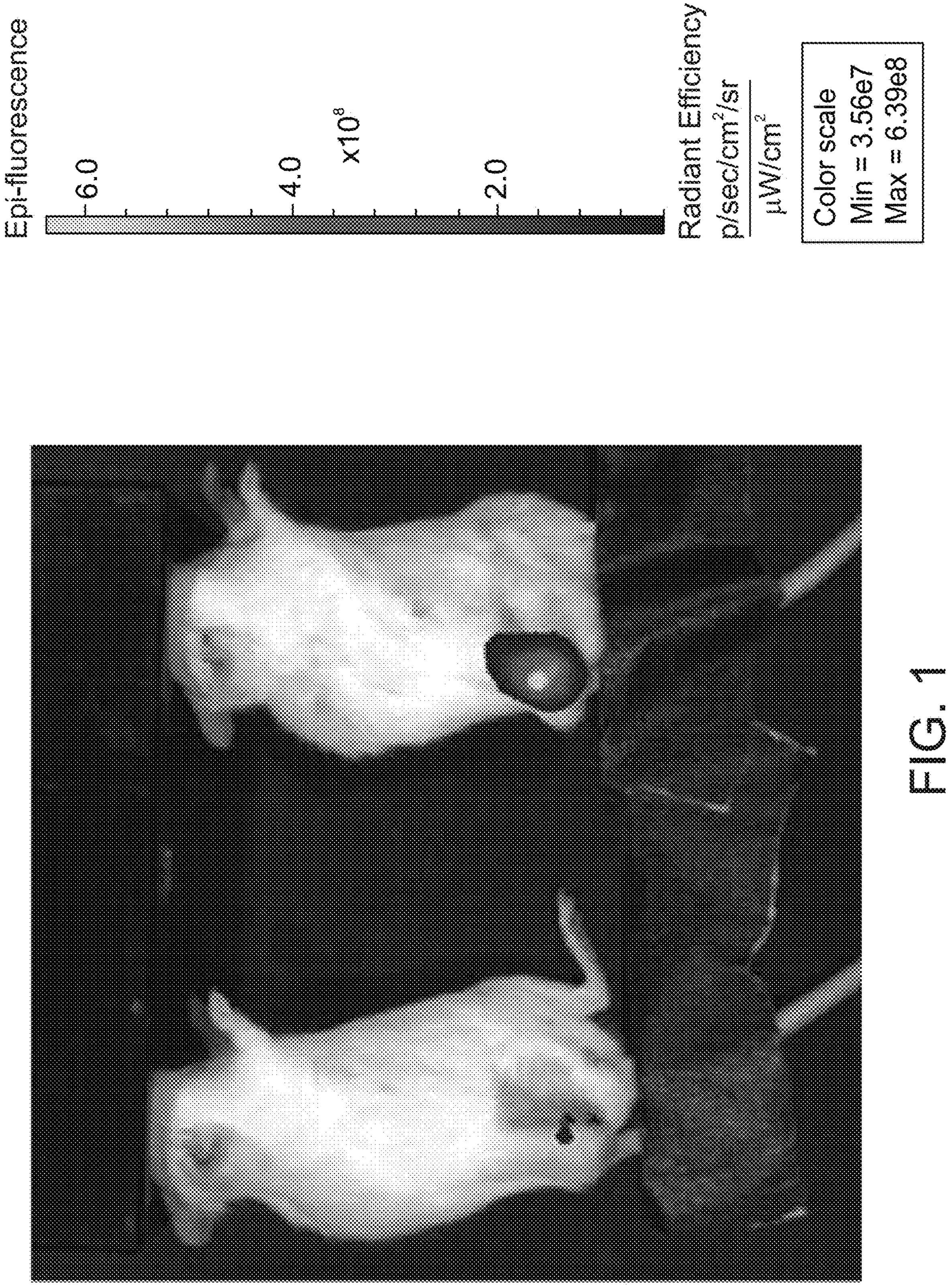
FIG. 1 presents an image showing intensity of fluorescence in mice 147 hours after intra-articular injection of fluorescent-labeled hyaluronic acid (mouse on left) or fluorescent-labeled hydrogenated soy phosphatidylcholine liposomes with pMPC moieties according to some embodiments of the invention; labeling was with the fluorescent dye DiR.

The present invention, in some embodiments thereof, relates to therapy, and more particularly, but not exclusively, to novel polymeric compounds usable, inter alia, for forming drug delivery vehicles.

Before explaining at least one embodiment of the invention in detail, it is to be understood that the invention is not necessarily limited in its application to the details set forth in the following description or exemplified by the Examples. The invention is capable of other embodiments or of being practiced or carried out in various ways.

While investigating liposomes in vivo, the present inventors have serendipitously found that liposomes stabilized with lipid-derived polymeric compounds, in which monomers include both phosphate and ammonium ionic groups, have particularly long retention times in vivo. As demonstrated in the Examples section that follows, the present inventors have uncovered that liposomes comprising such polymeric compound are suitable for drug delivery, and compare favorably with the state of the art PEGylated liposomes for drug delivery, for example, exhibiting longer retention times than comparable PEGylated liposomes.

Embodiments of the present invention therefore relate to the use of such liposome as drug delivery vehicles, that is, to liposomes incorporating therapeutically active agents and to uses thereon in treating medical conditions. In some embodiments, the liposomes are used for treating medical conditions in which prolonged retention times of the therapeutically active agent(s) in the liposome are desired or required.

According to an aspect of some embodiments of the invention, there is provided a liposome comprising at least one bilayer-forming lipid, a polymeric compound according to any of the respective embodiments described herein, and a therapeutically active agent incorporated in the liposome and/or on the liposome. The liposome, in some embodiments, is for use in delivering the therapeutically active agent to a subject in need thereof.

According to an aspect of some embodiments of the invention, there is provided a use of a liposome comprising at least one bilayer-forming lipid, a polymeric compound according to any of the respective embodiments described herein, and a therapeutically active agent incorporated in the liposome and/or on the liposome, in the manufacture of a medicament for use in delivering the therapeutically active agent to a subject in need thereof.

According to an aspect of some embodiments of the invention, there is provided a method of delivering a therapeutically active agent to a subject in need thereof, the method comprising administering to the subject a liposome comprising at least one bilayer-forming lipid, a polymeric compound according to any of the respective embodiments described herein, and a therapeutically active agent incorporated in the liposome and/or on the liposome, thereby delivering the therapeutically active agent to a subject in need thereof.

In some embodiments of any of the embodiments according to any of the aspects described herein, the use of the liposome and/or method described herein is for treating a medical condition treatable by the therapeutically active agent (according to any of the respective embodiments described herein) in the subject.

In some embodiments of any of the embodiments according to any of the aspects described herein, delivering the therapeutically active agent comprises sustained release of the therapeutically active agent according to any of the respective embodiments described herein.

In some embodiments of any of the embodiments according to any of the aspects described herein, the liposome is selected as capable of sustained release of the therapeutically active agent according to any of the respective embodiments described herein.

As used herein, "delivery" or "delivering" of a therapeutically active agent or drug (which terms are used herein interchangeably) refers to administration of the therapeutically active agent to a subject while controlling duration and/or proportion of the agent at a desired bodily site, depending on a subject's condition (e.g., a bodily site at which the agent desirably exerts a therapeutic effect). Thus, the terms "delivery" and "delivering" (and grammatical variations thereof) encompass targeting of a therapeutically active agent to a specific bodily site, such that a higher proportion of the agent reaches said bodily site (e.g., using a suitable targeting moiety); and/or control over duration of a presence of such an agent in the body (e.g., in the blood)—for example, by sustained release—which may be associated with a duration of such an agent at a desired bodily site (even if in the absence of specific targeting to the bodily site).

As used herein, "sustained release" refers to a formulation of an agent which provides a gradual and/or delayed ("sustained") release of the agent (e.g., from a reservoir such a liposome according to any of the respective embodiments described herein), which results in the agent being present in a bodily site (e.g., in the blood upon systemic administration, or in a bodily site to which the agent is locally administered) for a longer duration and/or at a later time (relative to administration) than if the agent is administered per se (via the same administration route).

For example, an agent administered per se (as opposed to a sustained release formulation) in the context of embodiments of the invention optionally refers to a formulation of the agent devoid of liposomes according to embodiments of the invention, and comprising the same carrier (if any) as the sustained release formulation.

In some embodiments, the sustained release is characterized by a concentration of therapeutically active agent (e.g., in the blood upon systemic administration, or in a bodily site to which the agent is locally administered) which is at least half of the maximal concentration (Cmax) for a time period which is at least 50% more than a corresponding time period (i.e., during which a concentration of an agent is at least half of the maximal concentration) an agent upon administration of the therapeutically effective agent per se (e.g., as defined herein) in an amount which results in the same maximal concentration. In some such embodiments, the time period (for sustained release) is at least 100% more than (i.e., twice) a corresponding time period (for the agent per se). In some embodiments, the time period (for sustained release) is at least 200% more than (i.e., 3-fold) a corresponding time period (for the agent per se). In some embodiments, the time period (for sustained release) is at least 400% more than (i.e., 5-fold) a corresponding time period (for the agent per se).

In some embodiments, the sustained release is characterized by a concentration of therapeutically active agent (e.g., in the blood upon systemic administration, or in a bodily site to which the agent is locally administered) which is at least half of the maximal concentration (Cmax) for a time period of at least 6 hours. In some such embodiments, the time period is at least 12 hours. In some embodiments, the time period is at least 24 hours. In some embodiments, the time period is at least 2 days. In some embodiments, the time period is at least 4 days. In some embodiments, the time period is at least one week. In some embodiments, the time period is at least 2 weeks. In some embodiments, the time period is at least 4 weeks.

Sustained release (according to any of the respective embodiments described herein), may allow, for example, for a regimen characterized by less frequent administration and/or by greater therapeutic efficacy of any given administration. The skilled person will be readily capable of determining a suitable frequency of administration for a given therapeutically active agent based on the duration of the sustained release (e.g., a time period during which the concentration of the agent is at least half of the maximal concentration, according to any of the respective embodiments described herein, and/or at least a minimal effective concentration), and the ratio between a desirable maximal concentration and a minimal effective concentration for the given agent (e.g., a "therapeutic window" of the agent).

Polymeric Compound:

According to some embodiments of any of the embodiments described herein, the polymeric compound comprised by a liposome (according to any of the respective embodiments described herein) has the general formula I:

Formula I

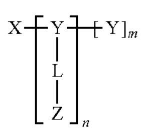

wherein:

m is zero or a positive integer;

n is an integer which is at least 1;

X is a lipid moiety, wherein when X does not comprise a phosphate group, n is at least 2;

Y is a backbone unit which forms a polymeric backbone;

L is absent or is a linking moiety; and

Z has the general formula II:

Formula II

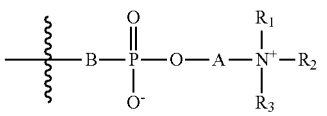

wherein:

A is a substituted or unsubstituted hydrocarbon;

B is an oxygen atom or is absent; and $R_1$-$R_3$ are each independently hydrogen, alkyl, cycloalkyl, heteroalicyclic, aryl or heteroaryl, as described in more detail herein below.

Formula I may also be described herein simply as:

$$X—[Y(—L—Z)]_{n}[Y]_{m}$$

which is to be regarded as interchangeable with the schematic depiction hereinabove.

Herein, the term "polymeric" refers a compound having at least 2 repeating units (and more preferably at least 3 repeating units), the repeating units being identical or similar. It is to be appreciated that the compound of general formula I is by definition polymeric when n is at least 2, as it comprises at least 2 of the backbone units represented by Y.

Herein, the phrase "polymeric moiety" refers to the portion of the polymeric compound (according to any of the embodiments described herein relating to general formula I) which has the general formula Ia:

Formula Ia

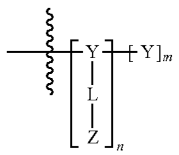

wherein m, n, Y, L and Z are as defined herein for general formula I.

Formula Ia may also be described herein simply as:

$$[Y(—L—Z)]_{n}[Y]_{m}$$

which is to be regarded as interchangeable with the schematic depiction hereinabove.

Herein, the phrase "polymeric compound" further encompasses compounds having a "polymeric moiety" as described herein having one unit (e.g., according to formula Ia wherein n is 1), provided that the lipid moiety described herein (e.g., the lipid moiety represented by X) has a similar unit. For example, when the lipid moiety comprises a phosphate group (e.g., the lipid moiety is a glycerophospholipid moiety), such that the lipid moiety has a phosphate group and a single unit of the polymeric moiety has a phosphate group, the two phosphate groups may be regarded as repeating units.

In preferred embodiments however, n is at least 2, such that the polymeric moiety per se has at least two units. In some embodiments, n is at least 3.

As used herein, the term "backbone unit" refers to a repeating unit, wherein linkage of a plurality of the repeating unit (e.g., sequential linkage) forms a polymeric backbone. A plurality of linked repeating units per se is also referred to herein as a "polymeric backbone".

As shown in formulas I and Ia, L and Z together form a pendant group of at least a portion of the backbone units, which group is referred to herein for brevity simply as the "pendant group".

Each backbone unit Y with pendant group (i.e., a unit represented by Y(-L-Z), the number of which is represented by the variable n) and each backbone unit Y without a pendant group (the number of which is represented by the variable m) is also referred to herein as a "monomeric unit".

A backbone unit may optionally be a residue of a polymerizable monomer or polymerizable moiety of a monomer. A wide variety of polymerizable monomers and moieties will be known to the skilled person, and the structure of the residues of such monomers which result upon polymerization (e.g., monomeric units) will also be known to the skilled person.

A "residue of a polymerizable monomer" refers to a modified form of a polymerizable monomer and/or a portion of a polymerizable monomer that remains after polymerization.

A portion of a polymerizable monomer may be formed, for example, by a condensation reaction, e.g., wherein at least one atom or group (e.g., a hydrogen atom or hydroxyl group) in the monomer, and optionally at least two atoms or groups (e.g., a hydrogen atom and a hydroxyl group) in the monomer, is replaced with a covalent bond with another polymerizable monomer.

A modified form of a polymerizable monomer may be formed, for example, by ring-opening (wherein a covalent bond between two atoms in a ring is broken, and the two atoms optionally each become linked to another polymerizable monomer); and/or by adding to an unsaturated bond, wherein an unsaturated bond between two adjacent atoms is broken (e.g., conversion of an unsaturated double bond to a saturated bond, or conversion of an unsaturated triple bond to an unsaturated double bond) and the two atoms optionally each become linked to another polymerizable monomer.

A modified form of a polymerizable monomer may consist essentially of the same atoms as the original monomer, for example, different merely in the rearrangement of covalent bonds, or alternatively, may have a different atomic composition, for example, wherein polymerization includes a condensation reaction (e.g., as described herein).

Examples of backbone units include, without limitation, substituted or unsubstituted hydrocarbons (which may form a substituted or unsubstituted hydrocarbon backbone), such as alkylene units; hydroxycarboxylic acid units (which may form a polyester backbone), e.g., glycolate, lactate, hydroxybutyrate, hydroxyvalerate, hydroxycaproate and hydroxybenzoate units; dicarboxylic acid units (which may form a polyester backbone in combination with a diol and/or a polyamide in combination with a diamine), e.g., adipate, succinate, terephthalate and naphthalene dicarboxylic acid units; diol units (which may form a polyether backbone, or form a polyester backbone in combination with a dicarboxylic acid), e.g., ethylene glycol, 1,2-propanediol, 1,3-propanediol, 1,4-butanediol, and bisphenol A units; diamine units (which may form a polyamide backbone in combination with a dicarboxylic acid), e.g., para-phenylene diamine and alkylene diamines such hexylene diamine; carbamate units (which may form a polyurethane backbone); amino acid residues (which may form a polypeptide backbone); and saccharide residues (which may form a polysaccharide backbone).

In some embodiments of any of the embodiments described herein, Y is a substituted or unsubstituted alkylene unit.

In some embodiments, Y is a substituted or unsubstituted ethylene unit, that is, an alkylene unit 2 atoms in length.

Polymeric backbones wherein Y is a substituted or unsubstituted ethylene unit may optionally be a polymeric backbone such as formed by polymerizing ethylene ($CH_2{=}CH_2$) and/or substituted derivatives thereof (also referred to herein as "vinyl monomers"). Such polymerization is a very well-studied procedure, and one of ordinary skill in the art will be aware of numerous techniques for effecting such polymerization.

It is to be understood that any embodiments described herein relating to a polymeric backbone formed by a polymerization encompass any polymeric backbone having a structure which can be formed by such polymerization, regardless of whether the polymeric backbone was formed in practice by such polymerization (or any other type of polymerization).

As is well known in the art, the unsaturated bond of ethylene and substituted ethylene derivatives becomes saturated upon polymerization, such that the backbone units in a polymeric backbone are saturated, although they may be referred to as units of an unsaturated compound (e.g., a "vinyl monomer" or "olefin monomer") to which they are analogous.

Polymers which can be formed from unsaturated monomers such as vinyl monomers and olefin monomers are also referred to by the terms "polyvinyl" and "polyolefin".

Herein, an "unsubstituted" alkylene unit (e.g., ethylene unit) refers to an alkylene unit which does not have any substituent other than the pendant group discussed herein (represented as (-L-Z)). That is, an alkylene unit attached to the aforementioned pendant group is considered unsubstituted if there are no substituents at any other positions on the alkylene unit.

In some embodiments of any of the embodiments described herein, Y has the formula $—CR_4R_5—CR_6D$-.

When Y is a backbone unit which is not attached to L or Z (i.e., to a pendant group described herein), D is $R_7$ (an end group, as defined herein); and when Y is a backbone unit which is attached to L or Z, D is a covalent bond or a linking group attaching Y to L or Z. The linking group may optionally be —O—, —S—, arylene, sulfinyl, sulfonyl, phosphate, phosphonyl, phosphinyl, carbonyl, thiocarbonyl, urea, thiourea, O-carbamyl, N-carbamyl, O-thiocarbamyl, N-thiocarbamyl, C-amido, N-amido, C-carboxy, O-carboxy, sulfonamido, or amino.

$R_4$-$R_7$ are each independently hydrogen, alkenyl, alkynyl, cycloalkyl, aryl, heteroaryl, heteroalicyclic, halo, hydroxy, alkoxy, aryloxy, thiohydroxy, thioalkoxy, thioaryloxy, sulfinyl, sulfonyl, cyano, nitro, azide, azo, phosphate phosphonyl, phosphinyl, oxo, carbonyl, thiocarbonyl, urea, thiourea, O-carbamyl, N-carbamyl, O-thiocarbamyl, N-thiocarbamyl, C-amido, N-amido, C-carboxy, O-carboxy, sulfonamido, or amino.

Herein, the phrase "linking group" describes a group (e.g., a substituent) that is attached to two or more moieties in the compound.

Herein, the phrase "end group" describes a group (e.g., a substituent) that is attached to a single moiety in the compound via one atom thereof.

When each of $R_4$-$R_6$ is hydrogen, and D is a covalent bond or linking group, Y is an unsubstituted ethylene group attached (via D) to a pendant group described herein.

When each of $R_4$-$R_7$ is hydrogen (and D is $R_7$), Y is an unsubstituted ethylene group which is not attached to a pendant group described herein.

In some embodiments of any of the embodiments described herein, $R_4$ and $R_5$ are each hydrogen. Such embodiments include polymeric backbones formed from many widely used vinyl monomers (including ethylene), including, for example, olefins (e.g., ethylene, propylene, 1-butylene, isobutylene, 4-methyl-1-pentene), vinyl chloride, styrene, vinyl acetate, acrylonitrile, acrylate and derivatives thereof (e.g., acrylate esters, acrylamides), and methacrylate and derivatives thereof (e.g., methacrylate esters, methacrylamides).

In some embodiments of any of the embodiments described herein, $R_6$ is hydrogen. In some such embodiments, $R_4$ and $R_5$ are each hydrogen.

In some embodiments of any of the embodiments described herein, $R_6$ is methyl. In some such embodiments, $R_4$ and $R_5$ are each hydrogen. In some such embodiments, the backbone unit is a unit of methacrylate or a derivative thereof (e.g., methacrylate ester, methacrylamide).

In some embodiments of any of the embodiments described herein, the linking group represented by the variable D is —O—, —C(═O)O—, —C(═O)NH— or phenylene. In exemplary embodiments, D is —C(═O)O—.

For example, the backbone unit may optionally be a vinyl alcohol derivative (e.g., an ester or ether of a vinyl alcohol unit) when D is —O—; an acrylate or methacrylate derivative (e.g., an ester of an acrylate or methacrylate unit) when D is —C(═O)O—; an acrylamide or methacrylamide unit when D is —C(═O)NH—; and/or a styrene derivative (e.g., a substituted styrene unit) when D is phenylene.

In some embodiments of any of the embodiments described herein, L is a substituted or unsubstituted hydrocarbon from 1 to 10 carbon atoms in length. In some embodiments, the hydrocarbon is unsubstituted. In some embodiments, the hydrocarbon is a linear, unsubstituted hydrocarbon; that is, $—(CH_2)_i—$ wherein i is an integer from 1 to 10.

In some embodiments of any of the embodiments described herein, L is a substituted or unsubstituted ethylene group. In some embodiments, L is an unsubstituted ethylene group ($—CH_2CH_2—$).

In some embodiments of any of the embodiments described herein, B is an oxygen atom. In some such embodiments, L is a hydrocarbon according to any of the respective embodiments described herein (i.e., L is not absent), and Z is a phosphate group attached to L.

In some embodiments of any of the embodiments described herein, B is absent. In some such embodiments, L is a hydrocarbon according to any of the respective embodiments described herein (i.e., L is not absent), and Z is a phosphonate group attached to L. In some embodiments, L is also absent, such that the phosphorus atom of formula II is attached directly to Y.

In some embodiments of any of the embodiments described herein, A is a substituted or unsubstituted hydrocarbon from 1 to 4 carbon atoms in length.

In some embodiments of any of the embodiments described herein, A is an unsubstituted hydrocarbon. In some such embodiments, the unsubstituted hydrocarbon is from 1 to 4 carbon atoms in length. In some embodiments, the hydrocarbon is a linear, unsubstituted hydrocarbon; that is, $—(CH_2)_j—$ wherein j is an integer from 1 to 4.

In some embodiments of any of the embodiments described herein, A is a substituted or unsubstituted ethylene group.

In some embodiments of any of the embodiments described herein, A is an unsubstituted ethylene group ($—CH_2CH_2—$). In such embodiments, the moiety having general formula II (represented by the variable Z) is similar or identical to a phosphoethanolamine or phosphocholine moiety. Phosphoethanolamine and phosphocholine moieties are present in many naturally occurring compounds (e.g., phosphatidylcholines, phosphatidylethanolamines).

In some embodiments of any of the embodiments described herein, A is an ethylene group substituted by a C-carboxy group. In some embodiments, the C-carboxy is attached to the carbon atom adjacent to the nitrogen atom depicted in formula II (rather than the carbon atom attached to the depicted oxygen atom). In such embodiments, the moiety having general formula II (represented by the variable Z) is similar or identical to a phosphoserine moiety. Phosphoserine is present in many naturally occurring compounds (e.g., phosphatidylserines).

Without being bound by any particular theory, it is believed that moieties similar or identical to naturally occurring moieties such as phosphocholine, phosphoethanolamine and/or phosphoserine may be particularly biocompatible.

In some embodiments of any of the embodiments described herein, $R_1$-$R_3$ (the substituents of the nitrogen atom depicted in general formula II) are each independently hydrogen or $C_{1-4}$-alkyl. In some embodiments, $R_1$-$R_3$ are each independently hydrogen or methyl. In some embodiments, $R_1$-$R_3$ are each methyl. In some such embodiments, $R_1$-$R_3$ are each hydrogen.

The variable n may be regarded as representing a number of backbone units (represented by the variable Y) which are substituted by the pendant group represented by (-L-Z), and the variable m may be regarded as representing a number of backbone units which are not substituted by such a pendant group. The sum n+m may be regarded as representing the total number of backbone units in the polymeric backbone. The ratio n/(n+m) may be regarded as representing the fraction of backbone units which are substituted by the pendant group represented by (-L-Z).

The backbone unit Y substituted by the pendant group may be the same as or different than the backbone unit Y which is not substituted by the pendant group (e.g., when m is at least 1).

The plurality (indicated by the variable n) of backbone units Y substituted by the pendant group may be the same as each other or different from each other.

In addition, the plurality (indicated by the variable n) of pendant groups (-L-Z) attached to a plurality of backbone units Y may be the same as each other or different from each other (e.g., may differ in the identity of any one or more of A, B, $R_1$, $R_2$, $R_3$ and L).

In any of the embodiments described herein wherein more than one backbone unit Y is not substituted by the pendant group described herein (i.e., when m is more than 1), the plurality (indicated by the variable m) of backbone units Y which are substituted by the pendant group may be the same as each other or different from each other.

The number of types of backbone units substituted by the pendant group, the number of types of backbone units not substituted by the pendant group (if any such units are present), and/or the number of types of pendant group in the polymeric moiety may each independently be any number (e.g., 1, 2, 3, 4, 5, 6, 7, 8, 9, 10 or more).

In some embodiments of any of the embodiments described herein, the polymeric moiety is a copolymer moiety, that is, the polymeric moiety comprises at least two different types of monomeric unit. The different types of monomeric unit may differ in whether they comprise the pendant group (-L-Z) according to any of the respective embodiments described herein (e.g., when m is at least 1), differ in the type of backbone unit Y, and/or differ in the type of pendant group (-L-Z).

For example, in some embodiments of any of the embodiments described herein the backbone unit Y in each of the Y(-L-Z) units may optionally be the same or different, while the L and Z moieties are the same among the Y(-L-Z) units. In some such embodiments, backbone units not substituted by the pendant group (if any such units are present) may optionally be the same as backbone unit Y in each of the Y(-L-Z) units. Alternatively, backbone units not substituted by the pendant group (if any such units are present) may optionally be different than backbone unit Y in each of the Y(-L-Z) units (while optionally being the same among all backbone units not substituted by the pendant group).

In some embodiments of any of the embodiments described herein the L moiety in each of the Y(-L-Z) units may optionally be the same or different, while the backbone units Y and the Z moieties are the same among the Y(-L-Z) units. In some such embodiments, backbone units not substituted by the pendant group (if any such units are present) may optionally be the same as backbone unit Y in each of the Y(-L-Z) units. Alternatively, backbone units not substituted by the pendant group (if any such units are present) may optionally be different than backbone unit Y in each of the Y(-L-Z) units (while optionally being the same among all backbone units not substituted by the pendant group).

In some embodiments of any of the embodiments described herein the Z moiety in each of the Y(-L-Z) units may optionally be the same or different, while the backbone units Y and the Z moieties are the same among the Y(-L-Z) units. In some such embodiments, backbone units not substituted by the pendant group (if any such units are present) may optionally be the same as backbone unit Y in each of the Y(-L-Z) units. Alternatively, backbone units not substituted by the pendant group (if any such units are present) may optionally be different than backbone unit Y in each of the Y(-L-Z) units (while optionally being the same among all backbone units not substituted by the pendant group).

In any of the embodiments described herein wherein the polymeric moiety is a copolymer moiety, any two or more different types of monomeric unit may be distributed randomly or non-randomly throughout the polymeric moiety. When different types of monomeric unit are distributed non-randomly, the copolymer may be one characterized by any non-random distribution, for example, an alternating copolymer, a periodic copolymer, and/or a block copolymer.

In some embodiments of any of the embodiments described herein, at least a portion of the monomeric units of the polymeric moiety comprise a targeting moiety (according to any of the embodiments described herein relating to a targeting moiety).

A targeting moiety may optionally be comprised by a backbone unit Y according to any of the respective embodiments described herein, linking moiety L according to any of the respective embodiments described herein, and/or moiety Z according to any of the respective embodiments described herein, for example, wherein a substituent according to any of the respective embodiments described herein comprises (and optionally consists of) the targeting moiety. For example, in some embodiments wherein at least a portion of backbone units Y have the formula —$CR_4R_5$—$CR_6$D- (as described herein in any of the respective embodiments), any one or more of $R_4$-$R_6$ and D (optionally wherein D is $R_7$ as described herein) comprises a targeting moiety according to any of the respective embodiments described herein (e.g., wherein any one or more of $R_4$-$R_6$ and D is a substituted group, comprising a substituent which is a targeting moiety), and optionally any one or more $R_4$-$R_6$ and D is a targeting moiety. However, many other structures of monomeric units comprising a substituent which comprises (and optionally consist of) a targeting moiety are also encompassed by embodiments of the invention.

When Y is a backbone unit which is not attached to L or Z (i.e., to a pendant group as described herein), D is $R_7$ (an end group, as defined herein); and when Y is a backbone unit which is attached to L or Z, D is a covalent bond or a linking group attaching Y to L or Z. The linking group may optionally be —O—, —S—, arylene, sulfinyl, sulfonyl, phosphate, phosphonyl, phosphinyl, carbonyl, thiocarbonyl, urea, thiourea, O-carbamyl, N-carbamyl, O-thiocarbamyl, N-thiocarbamyl, C-amido, N-amido, C-carboxy, O-carboxy, sulfonamido, or amino.

$R_4$-$R_7$ are each independently hydrogen, alkenyl, alkynyl, cycloalkyl, aryl, heteroaryl, heteroalicyclic, halo, hydroxy, alkoxy, aryloxy, thiohydroxy, thioalkoxy, thioaryloxy, sulfinyl, sulfonyl, cyano, nitro, azide, azo, phosphate phosphonyl, phosphinyl, oxo, carbonyl, thiocarbonyl, urea, thiourea, O-carbamyl, N-carbamyl, O-thiocarbamyl, N-thiocarbamyl, C-amido, N-amido, C-carboxy, O-carboxy, sulfonamido, or amino.

In some embodiments, the polymeric moiety is a copolymer moiety wherein at least one type of monomeric unit comprises a targeting moiety (according to any of the respective embodiments described herein) and at least one type of monomeric unit does not comprise such a targeting moiety. The distribution of a monomeric unit comprising a targeting moiety may be in accordance with any distribution described herein of a monomeric unit in a copolymer moiety (e.g., random, alternating, periodic copolymer, and/or block copolymer).

In some embodiments of any of the embodiments described herein wherein a portion of monomeric units comprise a targeting moiety, the monomeric units comprising a targeting moiety are, on average, closer to a terminus of the polymeric moiety distal to the lipid moiety, e.g., an average distance (as measured in atoms or backbone units along the backbone of the polymeric moiety) of monomeric units comprising a targeting moiety from the lipid moiety is greater than an average distance of the other monomeric units from the lipid moiety.

In some embodiments, at least a portion (and optionally all) of the monomeric units comprising a targeting moiety form a block (of one or more monomeric units) near (and optionally at) a terminus of the polymeric moiety distal to the lipid moiety. In some such embodiments, the copolymer moiety contains a single monomeric unit which comprises a targeting moiety, and said monomeric unit is at a terminus of the polymeric moiety distal to the lipid moiety.

Without being bound by any particular theory, it is assumed that a targeting moiety located distal to the lipid moiety may be more effective as a targeting moiety (e.g., more effective at binding to a target), for example, due to the targeting moiety being less sterically shielded (e.g., by a surface to which the lipid moiety is associated) and therefore more exposed to and thus better able to make contact with targets in an aqueous environment.

In alternative embodiments, the polymeric moiety does not comprise a targeting moiety described herein according to any of the respective embodiments.

In some embodiments of any of the embodiments described herein, the percentage of backbone units (represented by the variable Y) which are substituted by the pendant group represented by (-L-Z) (as represented by the formula 100%*n/(n+m)) is at least 20%. In some embodiments, the percentage of backbone units substituted by the aforementioned pendant group is at least 30%. In some embodiments, the percentage of backbone units substituted by the aforementioned pendant group is at least 40%. In some embodiments, the percentage of backbone units substituted by the aforementioned pendant group is at least 50%. In some embodiments, the percentage of backbone units substituted by the aforementioned pendant group is at least 60%. In some embodiments, the percentage of backbone units substituted by the aforementioned pendant group is at least 70%. In some embodiments, the percentage of backbone units substituted by the aforementioned pendant group is at least 80%. In some embodiments, the percentage of backbone units substituted by the aforementioned pendant group is at least 90%. In some embodiments, the percentage of backbone units substituted by the aforementioned pendant group is at least 95%. In some embodiments, the percentage of backbone units substituted by the aforementioned pendant group is at least 98%.

In some embodiments of any of the embodiments described herein, m is 0, such that each of the backbone units (represented by the variable Y) is substituted by the pendant group represented by (-L-Z).

In some embodiments of any of the embodiments described herein, n is at least 5. In some embodiments, n is at least 10. In some embodiments, n is at least 15.

In some embodiments of any of the embodiments described herein, n is in a range of from 2 to 1,000. In some embodiments of any of the embodiments described herein, n is in a range of from 2 to 500. In some embodiments of any of the embodiments described herein, n is in a range of from 2 to 200. In some embodiments of any of the embodiments described herein, n is in a range of from 2 to 100. In some embodiments of any of the embodiments described herein, n is in a range of from 2 to 50. In some such embodiments, m is 0.

In some embodiments of any of the embodiments described herein, n is in a range of from 3 to 1,000. In some embodiments of any of the embodiments described herein, n is in a range of from 3 to 500. In some embodiments of any of the embodiments described herein, n is in a range of from 3 to 200. In some embodiments of any of the embodiments described herein, n is in a range of from 3 to 100. In some embodiments of any of the embodiments described herein, n is in a range of from 3 to 50. In some embodiments of any of the embodiments described herein, n is in a range of from 5 to 50. In some embodiments of any of the embodiments described herein, n is in a range of from 10 to 50. In some embodiments of any of the embodiments described herein, n is in a range of from 10 to 25. In some such embodiments, m is 0.

In some embodiments of any of the embodiments described herein, m is in a range of from 0 to 1,000. In some such embodiments, n is in a range of from 2 to 1,000, such that the total number of backbone units is in a range of from 2 to 2,000. In some such embodiments, n is in a range of from 3 to 1,000. In some embodiments, n is in a range of from 3 to 500. In some embodiments, n is in a range of from 3 to 200. In some embodiments, n is in a range of from 3 to 100. In some embodiments, n is in a range of from 3 to 50. In some embodiments, n is in a range of from 5 to 50. In some embodiments, n is in a range of from 10 to 50.

In some embodiments of any of the embodiments described herein, m is in a range of from 0 to 500. In some such embodiments, n is in a range of from 2 to 1,000. In some such embodiments, n is in a range of from 3 to 1,000. In some embodiments, n is in a range of from 3 to 500. In some embodiments, n is in a range of from 3 to 200. In some embodiments, n is in a range of from 3 to 100. In some embodiments, n is in a range of from 3 to 50. In some embodiments, n is in a range of from 5 to 50. In some embodiments, n is in a range of from 10 to 50.

In some embodiments of any of the embodiments described herein, m is in a range of from 0 to 200. In some such embodiments, n is in a range of from 2 to 1,000. In some such embodiments, n is in a range of from 3 to 1,000. In some embodiments, n is in a range of from 3 to 500. In some embodiments, n is in a range of from 3 to 200. In some embodiments, n is in a range of from 3 to 100. In some embodiments, n is in a range of from 3 to 50. In some embodiments, n is in a range of from 5 to 50. In some embodiments, n is in a range of from 10 to 50.

In some embodiments of any of the embodiments described herein, m is in a range of from 0 to 100. In some such embodiments, n is in a range of from 2 to 1,000. In some such embodiments, n is in a range of from 3 to 1,000. In some embodiments, n is in a range of from 3 to 500. In some embodiments, n is in a range of from 3 to 200. In some embodiments, n is in a range of from 3 to 100. In some embodiments, n is in a range of from 3 to 50. In some embodiments, n is in a range of from 5 to 50. In some embodiments, n is in a range of from 10 to 50.

In some embodiments of any of the embodiments described herein, m is in a range of from 0 to 50. In some such embodiments, n is in a range of from 2 to 1,000. In some such embodiments, n is in a range of from 3 to 1,000. In some embodiments, n is in a range of from 3 to 500. In some embodiments, n is in a range of from 3 to 200. In some embodiments, n is in a range of from 3 to 100. In some embodiments, n is in a range of from 3 to 50. In some embodiments, n is in a range of from 5 to 50. In some embodiments, n is in a range of from 10 to 50.

In some embodiments of any of the embodiments described herein, m is in a range of from 0 to 20. In some such embodiments, n is in a range of from 2 to 1,000. In some such embodiments, n is in a range of from 3 to 1,000. In some embodiments, n is in a range of from 3 to 500. In some embodiments, n is in a range of from 3 to 200. In some embodiments, n is in a range of from 3 to 100. In some embodiments, n is in a range of from 3 to 50. In some embodiments, n is in a range of from 5 to 50. In some embodiments, n is in a range of from 10 to 50.

In some embodiments of any of the embodiments described herein, m is in a range of from 0 to 10. In some such embodiments, n is in a range of from 2 to 1,000. In some such embodiments, n is in a range of from 3 to 1,000. In some embodiments, n is in a range of from 3 to 500. In some embodiments, n is in a range of from 3 to 200. In some embodiments, n is in a range of from 3 to 100. In some embodiments, n is in a range of from 3 to 50. In some embodiments, n is in a range of from 5 to 50. In some embodiments, n is in a range of from 10 to 50.

A lipid moiety (represented by the variable X in formula I herein) according to any of the embodiments herein may be attached to a polymeric moiety according to any of the embodiments described herein relating to the polymeric moiety.

The lipid moiety may optionally be derived from any lipid known in the art (including, but not limited to, a naturally occurring lipid). Derivation of the lipid moiety from the lipid may optionally consist of substituting a hydrogen atom at any position of the lipid with the polymeric moiety represented in general formula I by [Y(-L-Z)]n[Y]m (i.e., the polymeric moiety represented by general formula Ia).

In some embodiments of any of the embodiments described herein, the lipid moiety (according to any of the respective embodiments described herein) is attached to a Y(L-Z) unit (according to any of the embodiments described herein relating to Y, L and/or Z), that is, backbone unit substituted by the pendant group described herein (e.g., rather than a backbone unit not substituted by the pendant group).

Alternatively or additionally, in some embodiments of any of the embodiments described herein wherein m is at least 1, the lipid moiety (according to any of the respective embodiments described herein) may optionally be attached to a backbone unit (Y) which is not substituted by a pendant group described herein (e.g., rather than attached to a backbone unit substituted by the pendant group). For example, the polymeric moiety may optionally be a copolymer wherein the identity of the backbone unit attached to the lipid moiety varies randomly between molecules. Thus, the depiction of X in Formula I as being attached to a backbone unit substituted by a pendant group (i.e., Y-(L-Z)) rather than to an unsubstituted backbone unit Y is arbitrary, and is not intended to be limiting.

In some embodiments of any of the embodiments described herein, the lipid moiety is a moiety of a lipid which is a fatty acid, a monoglyceride, a diglyceride, a triglyceride, a glycerophospholipid, a sphingolipid, or a sterol. In some embodiments, the lipid is a glycerophospholipid.

In some embodiments of any of the embodiments described herein, the lipid moiety comprises at least one fatty acid moiety (e.g., an acyl group derived from a fatty acid). The fatty acid moiety may be derived from a saturated or unsaturated fatty acid. For example, the lipid moiety may consist of a fatty acid moiety, or be a monoglyceride moiety comprising one fatty acid moiety, a diglyceride moiety comprising two fatty acid moieties, or a triglyceride moiety comprising three fatty acid moieties.

Examples of fatty acid moieties which may optionally be comprised by the lipid moiety include, without limitation, lauroyl, myristoyl, palmitoyl, stearoyl, palmitoleoyl, oleoyl, and linoleoyl.

Suitable examples of glycerophospholipids include, without limitation, a phosphatidyl ethanolamine, a phosphatidyl serine, a phosphatidyl glycerol and a phosphatidyl inositol.

In some embodiments of any of the embodiments described herein, the lipid moiety represented by the variable X has the general formula III:

Formula III

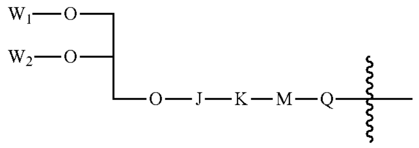

$W_1$ and $W_2$ are each independently hydrogen, alkyl, alkenyl, alkynyl or acyl, wherein at least one of $W_1$ and $W_2$ is not hydrogen;

J is —P(═O)(OH)—O—, or J is absent (such that K is attached directly to the depicted oxygen atom of a glycerol moiety);

K is a substituted or unsubstituted hydrocarbon from 1 to 10 carbon atoms in length, or K is absent (such that M is attached directly to J or, when J is absent, M is attached directly to the depicted oxygen atom of a glycerol moiety);

M is a linking group which is —O—, —S—, amino, sulfinyl, sulfonyl, phosphate, phosphonyl, phosphinyl, carbonyl, thiocarbonyl, urea, thiourea, carbamyl, thiocarbamyl, amido, carboxy, or sulfonamide, or M is absent; and Q is a substituted or unsubstituted hydrocarbon from 1 to 10 carbon atoms in length, and is attached to a backbone unit of the polymeric backbone according to any of the respective embodiments described herein.

When M is absent, K is also absent, and Q is attached directly to J or, when J is absent, Q is attached directly to the depicted oxygen atom of a glycerol moiety.

In some embodiments of any of the embodiments described herein, one of $W_1$ and $W_2$ is hydrogen and the other is not hydrogen.

In some embodiments of any of the embodiments described herein, neither $W_1$ nor $W_2$ is hydrogen.

In some embodiments of any of the embodiments described herein, at least one of $W_1$ and $W_2$ is an alkyl, alkenyl, alkynyl or acyl, which is from 10 to 30 carbon atoms in length. In some embodiments, each of $W_1$ and $W_2$ is from 10 to 30 carbon atoms in length.

Examples of acyl groups which may optionally serve independently as $W_1$ and/or $W_2$ include, without limitation, lauroyl, myristoyl, palmitoyl, stearoyl, palmitoleoyl, oleoyl, and linoleoyl.

In some embodiments of any of the embodiments described herein, J is —P(═O)(OH)—O— (e.g., the lipid moiety is a glycerophospholipid).

Herein, the length of the hydrocarbon represented by the variable K refers to the number of atoms separating J and M (i.e., along the shortest path between J and M) as depicted in formula III.

When K is a substituted hydrocarbon, M may be attached to a carbon atom of the hydrocarbon per se, or be attached to a substituent of the hydrocarbon.

In some embodiments of any of the embodiments described herein, K is an ethanolamine moiety (e.g., $—CH_2—CH_2—NH—$, or $—CH_2—CH_2—$ attached to a nitrogen atom), a serine moiety (e.g., $—CH_2—CH(CO_2H)—NH—$, or $—CH_2—CH(CO_2H)—$ attached to a nitrogen atom), a glycerol moiety (e.g., —CH(OH)—CH(OH)—CH—O—) and an inositol moiety (e.g., -cyclohexyl$(OH)_4$—O—). In some embodiments, J is —P(═O)(OH)—O—.

In some embodiments of any of the embodiments described herein, M is amido, optionally —C(═O)NH—.

In some embodiments, the nitrogen atom of the amido is attached to K. In some such embodiments, K is an ethanolamine or serine moiety described herein.

In some embodiments of any of the embodiments described herein, J is absent (e.g., wherein the glycerolipid is not a glycerophospholipid). In some such embodiments, K is also absent, such that M is attached directly to the depicted oxygen atom of a glycerol moiety or, when M is also absent, Q is attached directly to the depicted oxygen atom of a glycerol moiety (e.g., wherein the glycerolipid is a monoacylglycerol derivative or diacylglycerol derivative). In some embodiments, M is a carbonyl linking group, such that attachment of M to the aforementioned oxygen atom of the glycerol moiety is via an ester bond.

In some embodiments of any of the embodiments described herein, Q is a substituted or unsubstituted methylene group. In some such embodiments, M comprises a carbonyl (i.e., C(═O)) linking group. In some embodiments, M is amido (which comprises a carbonyl and a nitrogen atom. In some embodiments, the C(═O) (e.g., of the amido) is attached to Q. In some embodiments, M consists of a carbonyl linking group.

In some embodiments of any of the embodiments described herein, Q is a methylene group substituted by one or two substituents. In some embodiments, the methylene group is substituted by one or two alkyl groups (e.g., $C_{1-4}$-alkyl).

In some embodiments of any of the embodiments described herein, Q is a methylene group substituted by two substituents. In some embodiments, the methylene group is substituted by two alkyl groups (e.g., $C_{1-4}$-alkyl). In some embodiments, the alkyl groups are methyl, such that Q is dimethylmethylene ($—C(CH_3)_2—$).

As exemplified in the Examples section herein, a substituted methylene (e.g., di-substituted methylene) represented by the variable Q is particularly suitable for participating in polymerization reactions (e.g., as an initiator), because a free radical and/or ion on the methylene may be stabilized by the substituent(s) thereof.

As further exemplified herein, formation of an amido group (represented by the variable M) may serve as a convenient way to attach the abovementioned substituted methylene to a lipid (e.g., a naturally occurring lipid) such as a phosphatidylethanolamine or phosphatidylserine.

As further exemplified herein, formation of an ester bond between a carbonyl (e.g., comprised by M) and an oxygen atom of a lipid (e.g., an oxygen atom of a glycerol moiety) may serve as a convenient way to attach the abovementioned substituted methylene to a lipid (e.g., a naturally occurring lipid) such as a monoacylglycerol, diacylglycerol, phosphatidyl glycerol or phosphatidyl inositol.

Targeting Moiety:

As described hereinabove, in some embodiments of any of the embodiments described herein, at least a portion of the monomeric units comprise a targeting moiety (according to any of the embodiments described herein relating to a targeting moiety).

Herein, a "targeting moiety" refers to a moiety which is capable of bringing a compound (e.g., a compound according to some embodiments of the invention) into proximity with a selected substance and/or material (which is referred to herein as a "target"). The target is optionally a cell (e.g., a proliferating cell associated with the proliferative disease or disorder), wherein the proximity is such that the targeting moiety facilitates attachment and/or internalization of the compound into a target cell, and such that the compound may exert a therapeutic effect.

In any of the embodiments described herein wherein m is at least 1, at least a portion of the monomeric units comprising a targeting moiety (the number of which is represented by the variable m), according to any of the respective embodiments described herein, are monomeric units which do not comprise the pendant group represented by (-L-Z). In some such embodiments, each of the monomeric units comprising a targeting moiety (according to any of the respective embodiments described herein) is a monomeric unit which comprises the pendant group represented by (-L-Z) (i.e., a backbone unit Y substituted by (-L-Z)), that is, none of the monomeric units comprising the pendant group represented by (-L-Z) comprise the aforementioned targeting moiety.

In any of the embodiments described herein wherein m is at least 1, each of the monomeric units which do not comprise the pendant group represented by (-L-Z) (the number of which is represented by the variable m) comprises a targeting moiety (according to any of the respective embodiments described herein). In some such embodiments, each of the monomeric units comprising a targeting moiety (according to any of the respective embodiments described herein) is a monomeric unit which does not comprise the pendant group represented by (-L-Z), that is, none of the monomeric units comprising the pendant group represented by (-L-Z) comprise the aforementioned targeting moiety, and each of the monomeric units which does not comprise the pendant group represented by (-L-Z) comprises the aforementioned targeting moiety.

In any of the embodiments described herein wherein m is at least 1, a monomeric unit comprising a targeting moiety may consist essentially of a backbone unit Y (according to any of the respective embodiments described herein) substituted by one or more targeting moieties (according to any of the respective embodiments described herein).

The backbone unit Y of a monomeric unit comprising a targeting moiety may optionally be different (optionally considerably different) in structure than a backbone unit Y of other monomeric units in the polymeric moiety (according to any of the respective embodiments described herein).

In any of the embodiments described herein wherein m is at least 1, the polymeric moiety comprises a monomeric unit which comprises a targeting moiety, and said monomeric unit is at a terminus of the polymeric moiety distal to the lipid moiety. In such embodiments, the compound represented by general formula I has the formula Ib:

Formula Ib

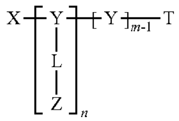

wherein:

T is a monomeric unit comprising a targeting moiety (according to any of the respective embodiments described herein);

X and T are attached to distal termini of the moiety represented by [Y(-L-Z)]n[Y]m−1; and X, Y, L, Z, n and m are defined in accordance with any of the embodiments described herein relating to general formula I, with the proviso that m is at least 1.

It is to be understood that T in formula Tb is a type of monomeric unit represented by Y (i.e., without the pendant group represented by (-L-Z)) in formulas I and Ia, and the number of monomeric units represented by Y (i.e., without the pendant group represented by (-L-Z)) other than T is represented by the value m−1, such that the total number of monomeric units without the pendant group represented by (-L-Z)), including T, is represented by the variable m, as in formulas I and Ia.

In some embodiments, m is 1, such that m−1 is zero, and the compound represented by formula Tb consequently has the formula: X—[Y(-L-Z)]n-T, wherein L, T, X, Y, Z and n are defined in accordance with any of the embodiments described herein.

A monomeric unit comprising a targeting moiety according to any of the respective embodiments described herein may optionally be prepared by preparing a monomer comprising a targeting moiety, and using said monomer to prepare a polymeric moiety described herein (e.g., by polymerization of monomers according to any of the respective embodiments described herein) and/or by modifying a monomeric unit in a polymeric moiety subsequently to preparation of a polymeric moiety (e.g., by polymerization of monomers according to any of the respective embodiments described herein), using any suitable technique known in the art, including, but not limited to, techniques for conjugation.

In some embodiments of any of the embodiments described herein relating to a targeting moiety, the targeting moiety does not comprise a moiety having general formula TT (according to any of the respective embodiments described herein). For example, even if a moiety represented by general formula II is capable of forming a bond with a target as described herein, the phrase "targeting moiety", in some embodiments, is to be understood as relating to a moiety distinct from a moiety represented by variable Z (having general formula II).

In some embodiments of any one of the embodiments described herein, the pendant group represented by (-L-Z) is selected so as not to form a bond with the target and/or so as not to include a structure and/or property of a targeting moiety as described herein in any one of the respective embodiments. For example, in embodiments wherein a targeting moiety comprising a nucleophilic group (according to any of the respective embodiments described herein)—for example, an amine group—is capable of forming a bond (e.g., covalent bond) with a target, the variable Z (having general formula II) is optionally selected such that the depicted amine/ammonium group is a tertiary amine/ammonium (i.e., no more than one of $R_1$-$R_3$ is hydrogen) or quaternary ammonium (i.e., none of $R_1$-$R_3$ is hydrogen), preferably a quaternary ammonium (e.g., comprising a trimethylamino group, such as in phosphocholine). Tertiary amine groups, and especially quaternary ammonium groups, may be significantly less reactive nucleophilic groups than primary and secondary amine groups.

In some embodiments of any of the embodiments described herein relating to a targeting moiety, the targeting moiety comprises (and optionally consists of) at least one functional group capable of forming a covalent bond or non-covalent bond (preferably a selective non-covalent bond) with a substance and/or material (which is referred to herein as a "target"), e.g., at a surface of the target (e.g., a surface of a cell and/or tissue).

Herein, the phrase "functional group" encompasses chemical groups and moieties of any size and any functionality described herein (for example, any functionality capable of forming a covalent bond or non-covalent bond with a target).

A non-covalent bond according to any of the respective embodiments described herein may optionally be effected by non-covalent interactions such as, without limitation, electrostatic attraction, hydrophobic bonds, hydrogen bonds, and aromatic interactions.

In some embodiments, the targeting moiety comprises a functional group capable of forming a non-covalent bond which is selective for the target, e.g., an affinity (e.g., as determined based on a dissociation constant) of the targeting moiety and/or functional group to the target is greater than an affinity of the of the targeting moiety and/or functional group to most (or all) other compounds capable of forming a non-covalent bond with the targeting moiety.

In some embodiments of any one of the embodiments described herein, the functional group(s) are capable of forming a covalent bond with one or more specific functional groups (e.g., hydroxy, amine, thiohydroxy and/or oxo groups) which are present on the target (e.g., a target according to any of the respective embodiments described herein).

Examples of functional groups (in a targeting moiety) capable of forming a covalent bond with a target (according to any of the respective embodiments described herein) and the type of covalent bonds they are capable of forming, include, without limitation:

- nucleophilic groups such as thiohydroxy, amine (e.g., primary or secondary amine) and hydroxy, which may form covalent bonds with, e.g., a nucleophilic leaving group (e.g., any nucleophilic group described herein), Michael acceptor (e.g., any Michael acceptor described herein), acyl halide, isocyanate and/or isothiocyanate (e.g., as described herein) in a target;
- nucleophilic leaving groups such as halo, azide ($—N_3$), sulfate, phosphate, sulfonyl (e.g. mesyl, tosyl), N-hydroxysuccinimide (NHS) (e.g. NHS esters), sulfo-N-hydroxysuccinimide, and anhydride, which may form covalent bonds with, e.g., a nucleophilic group (e.g., as described herein) in a target;
- Michael acceptors such as enones (e.g., maleimide, acrylate, methacrylate, acrylamide, methacrylamide), nitro groups and vinyl sulfone, which may form covalent bonds with, e.g., a nucleophilic group (e.g., as described herein) in a target, optionally thiohydroxy;
- dihydroxyphenyl groups (according to any of the respective embodiments described herein), which may form covalent bonds with, e.g., a nucleophilic group (e.g., as described herein) and/or a substituted or unsubstituted phenyl group (e.g., another dihydroxyphenyl group) in a target, as described herein;
- an acyl halide (—C(═O)-halogen), isocyanate (—NCO) and isothiocyanate (—N═C═S) group, which may form covalent bonds with, e.g., a nucleophilic group (e.g., as described herein) in a target;
- a carboxylate (—C(═O)OH) group, which may form a covalent bond with, e.g., a hydroxyl group in a target to form an ester bond and/or an amine group (e.g., primary amine) in a target to form an amide bond (optionally by reaction with a coupling reagent such as a carbodiimide); and/or a carboxylate group is in a target and may form an amide or ester bond with an amine or hydroxyl group, respectively, in the targeting moiety;
- an oxo group (optionally in an aldehyde group (—C(═O)H)), which may form a covalent imine bond with an amine group (e.g., a primary amine) in a target; and/or an oxo group (optionally in an aldehyde group) is in a target and may form a covalent imine bond with an amine groups in the targeting moiety; and/or
- thiohydroxy groups, which may form covalent disulfide (—S—S—) bonds with a thiohydroxy group in a target.

Modification of a monomer (e.g., prior to polymerization) or a monomeric unit of a polymeric moiety (e.g., subsequent to polymerization) to comprise any of the functional groups described herein may optionally be performed using any suitable technique for conjugation known in the art. The skilled person will be readily capable of selecting a suitable technique for any given molecule to be modified.

Herein, the term "dihydroxyphenyl" refers to an aryl group (as defined herein) which is a phenyl substituted by two hydroxyl groups at any positions thereof. The phenyl may optionally be substituted by additional substituents (which may optionally comprise additional hydroxyl groups), to thereby form a substituted dihydroxyphenyl group; or alternatively, the phenyl comprises no substituents other than the two hydroxyl groups, such that the dihydroxyphenyl group is an unsubstituted dihydroxyphenyl group.

In some embodiments of any one of the embodiments described herein, the dihydroxyphenyl group is an ortho-dihydroxyphenyl (wherein the hydroxyl groups are attached to the phenyl at adjacent positions) or a para-dihydroxyphenyl (wherein the hydroxyl groups are attached to opposite sides of the phenyl ring), each being a substituted or unsubstituted dihydroxyphenyl. In some such embodiments, the ortho-dihydroxyphenyl or para-dihydroxyphenyl is an unsubstituted dihydroxyphenyl.

A dihydroxyphenyl group according to any of the respective embodiments described herein may optionally bond covalently and/or non-covalently to a target according to any one or more attachment mechanism described for dihydroxyphenyl (catechol) groups in Lee et al. [*PNAS* 2006, 103:12999-13003], Brodie et al. [*Biomedical Materials* 2011, 6:015014] and/or International Patent Application PCT/IL2015/050606 (published as WO 2015/193888), the contents of each of which are incorporated in their entirety, and especially contents regarding bonds formed by dihydroxyphenyl (catechol) groups to surfaces.

In some embodiments of any one of the embodiments described herein, the functional group capable of forming a bond to a target is a functional group capable of forming a covalent bond with an amine group, optionally a primary amine group. In some such embodiments, the target comprises on or more amino acids or amino acid residues, for example, a peptide or polypeptide of any length (e.g., at least two amino acid residues, for example, proteins), and the amine groups may optionally be lysine side chain amine groups and/or N-terminal amine groups. In some embodiments, the target comprises an extracellular matrix protein, for example, collagen. In some embodiments, the target comprises cartilage (e.g., articular cartilage).

In some embodiments of any one of the embodiments described herein, the targeting moiety comprises (and optionally consists of) at least one functional group capable of forming a non-covalent bond with the target (e.g., as described herein in any one of the respective embodiments).

In some embodiments of any one of the embodiments described herein, a functional group capable of forming a non-covalent bond with the target comprises (and optionally consists of) a polysaccharide and/or polypeptide (e.g., a protein and/or fragment thereof), wherein the target optionally comprises a ligand of the polysaccharide and/or polypeptide; and/or the target comprises a polysaccharide and/or polypeptide (e.g., a protein and/or fragment thereof) and the functional group capable of forming a non-covalent bond with the target is a ligand of the polysaccharide and/or polypeptide.

Examples of suitable polysaccharides and/or polypeptides, and ligands thereof, include, without limitation:

- avidin or streptavidin as a polypeptide described herein, and biotin as a ligand thereof;
- a polysaccharide-binding polypeptide as a polypeptide described therein, and a complementary polysaccharide as a ligand thereof (or a complementary polysaccharide-binding polypeptide as a ligand of a polysaccharide described herein);
- a collagen-binding polypeptide as a polypeptide described therein, and a complementary collagen as a ligand thereof (or a collagen as a polypeptide described herein and a complementary collagen-binding polypeptide as a ligand thereof);
- a cell receptor expressed by a cell, and a ligand selectively bound by the receptor;
- an antibody towards any antigen (e.g., wherein the target described herein optionally comprises the antigen) or a fragment of such an antibody as a polypeptide described herein, and the respective antigen as a ligand thereof; and
- an antibody mimetic towards any antigen (e.g., wherein the target described herein optionally comprises the antigen).

Examples of cell receptors expressed by a cell include, without limitation, receptors characteristic of a particular type of cell and/or tissue, and receptors overexpressed by a cancer cell. The cell receptor or the cell is optionally a target described herein, and the targeting moiety optionally comprises any ligand of the receptor. Examples of such ligands include, without limitation, transferrin, a ligand of transferrin receptor which may optionally target transferrin receptor overexpressed by some cancer cells; keratinocyte growth factor (KGF or FGF7) which is specific for cells of epithelial origin, and may optionally target KGF receptor such as that overexpressed by an endometrial carcinoma or pancreatic carcinoma [Visco et al., *Int J Oncol* 1999, 15:431-435; Siegfried et al., *Cancer* 1997, 79:1166-1171]; and epidermal growth factor (EGF) which may optionally target an EGF receptor, optionally an erbB, such as that overexpressed by gliomas and endometrial carcinomas [Normanno et al., *Curr Drug Targets* 2005, 6:243-257]).

As used herein, the term "antibody" encompasses any type of immunoglobin.

As used herein, the phrase "antibody mimetic" encompasses any type of molecule, optionally a polypeptide, referred as such in the art capable of selectively binding an antigen (e.g., non-covalently). Non-limiting examples of antibody mimetics include affibodies, affilins, affimers, affitins, alphabodies, anticalins, avimers, DARPins, Fynomers, Kunitz domain peptides, and monobodies, e.g., as described in Nygren [*FEBS J* 2008, 275:2668-2676], Ebersbach et al. [*J Mol Biol* 2007, 372:172-185], Johnson et al. [*Anal Chem* 2012, 84:6553-6560], Krehenbrink et al. [*J Mol Biol* 2008, 383:1058-1068], Desmet et al. [*Nature Comm* 2014, 5:5237], Skerra [*FEBS J* 2008, 275:2677-2683], Silverman et al. [*Nature Biotechnol* 2005, 23:1556-1561], Stumpp et al. [*Drug Discov Today* 2008, 13:695-701], Grabulovski et al. [*J Biol Chem* 2007, 282:3196-3204], Nixon & Wood [*Curr Opin Drug Discov Devel* 2006, 9:261-268], Koide & Koide [*Methods Mol Biol* 2007, 325:95-109], and Gebauer & Skerra [*Curr Opin Chem Biol* 2009, 13:245-255], the contents of each of which are incorporated in their entirety, and especially contents regarding particular types of antibody mimetics.

As used herein, the phrase "polysaccharide-binding polypeptide" encompasses any polypeptide or oligopeptide (peptide chains of at least 2, and preferably at least 4 amino acid residues in length) capable of selectively binding (e.g., non-covalently) to a polysaccharide. A wide variety of polysaccharide-binding polypeptides and their binding specificities will be known to the skilled person, and include short peptide sequences (e.g., from 4 to 50, optionally 4 to 20 amino acid residues in length), and longer polypeptides such as proteins or fragments (e.g., carbohydrate-binding modules and/or domains) thereof. In addition, the phrase "polysaccharide-binding polypeptide" encompasses antibodies capable of specifically binding to a polysaccharide. Such antibodies will be available to the skilled person and/or the skilled person will know how to prepare such antibodies, using immunological techniques known in the art.

Examples of polysaccharide-binding polypeptides which may be used in some of any one of the embodiments of the invention include, without limitation, carbohydrate-binding modules (CBMs); and hyaluronic acid-binding peptides, polypeptides and/or modules (e.g., having a sequence as described in any of International Patent Application publication WO 2013/110056; International Patent Application publication WO 2014/071132; Barta et al. [*Biochem J* 1993, 292:947-949], Kohda et al. [*Cell* 1996, 86:767-775], Brisset & Perkins [*FEBS Lett* 1996, 388:211-216], Peach et al. [*J Cell Biol* 1993, 122:257-264], Singh et al. [*Nature Materials* 2014, 13:988-995], and Zaleski et al. [*Antimicrob Agents Chemother* 2006, 50:3856-3860], the contents of each of which are incorporated in their entirety, and especially contents regarding particular polysaccharide-binding polypeptides), for example, GAHWQFNALTVR (SEQ ID NO: 1) (a hyaluronic acid-binding peptide sequence).

Examples of CBMs which may be used in some of any one of the embodiments of the invention, include, without limitation, CBMs belonging to the families CBM3, CBM4, CBM9, CBM10, CBM17 and/or CBM28 (which may optionally be used to bind cellulose, e.g., in a cellulose-containing target); CBM5, CBM12, CBM14, CBM18, CBM19 and/or CBM33 (which may optionally be used to bind chitin and/or other polysaccharides comprising N-acetylglucosamine, e.g., in a chitin-containing target); CBM15 (which may optionally be used to bind hemicellulose, e.g., in a hemicellulose-containing target); and/or CBM20, CBM21 and/or CBM48 (which may optionally be used to bind starch and/or glycogen, e.g., in a starch-containing and/or glycogen-containing target).

As used herein, the phrase "collagen-binding polypeptide" encompasses any polypeptide or oligopeptide (peptide chains of at least 2, and preferably at least 4 amino acid residues in length) capable of selectively binding (e.g., non-covalently) to a collagen (e.g., one type of collagen, some types of collagen, all types of collagen), including glycosylated polypeptides and oligopeptides such as peptidoglycans and proteoglycans. A wide variety of collagen-binding polypeptides and their binding specificities will be known to the skilled person, and include short peptide sequences (e.g., from 4 to 50, optionally 4 to 20 amino acid residues in length), and longer polypeptides such as proteins or fragments (e.g., collagen-binding domains) thereof. In addition, the phrase "collagen-binding polypeptide" encompasses antibodies capable of specifically binding to a collagen. Such antibodies will be available to the skilled person and/or the skilled person will know how to prepare such antibodies, using immunological techniques known in the art.

Examples of collagen-binding polypeptides which may be used in embodiments of the invention include, without limitation, collagen-binding proteins (e.g., decorin), fragments thereof and/or other polypeptides as described in U.S. Pat. No. 8,440,618, Abd-Elgaliel & Tung [*Biopolymers* 2013, 100:167-173], Paderi et al. [*Tissue Eng Part A* 2009, 15:2991-2999], Rothenfluh et al. [*Nat Mater* 2008, 7:248-254] and Helms et al. [*J Am Chem Soc* 2009, 131:11683-11685] (the contents of each of which are incorporated in their entirety, and especially contents regarding particular collagen-binding polypeptides), for example, the sequence WYRGRL (SEQ ID NO: 2).

It is expected that during the life of a patent maturing from this application many relevant functional groups and moieties for binding will be developed and/or uncovered and the scope of the terms "targeting moiety", "functional group", "cell receptor", "antibody", "antibody mimetic", "collagen-binding polypeptide" and "polysaccharide-binding polypeptide" and the like is intended to include all such new technologies a priori.

In some embodiments of any of the embodiments described herein, a functional group in a targeting moiety (according to any of the respective embodiments described herein) is attached to a linking group (as defined herein). The linking group may optionally be any linking group or linking moiety described herein, including, without limitation, a substituted or unsubstituted hydrocarbon. In some embodiments, the targeting moiety (optionally a substituent of a backbone unit Y) consists essentially of a functional group attached to the rest of the polymeric moiety via the linking group.

A functional group may optionally be attached to the linking moiety by a covalent bond obtainable by a reaction between two functional groups, for example, any covalent bond and/or functional groups described herein in the context of forming a covalent bond between a functional group and a target.

In some embodiments of any of the embodiments described herein relating to a functional group comprising a peptide or polypeptide, an amino acid residue of the peptide or polypeptide is optionally attached to a linking group of the targeting moiety, for example, via an amide bond formed from an amine or carboxylate group in the peptide or polypeptide (e.g., in an N-terminus, a lysine side chain, a C-terminus, a glutamate side chain and/or an aspartate side chain), an ester bond formed from a hydroxyl or carboxylate group in the peptide or polypeptide (e.g., in a serine side chain, a threonine side chain, a C-terminus, a glutamate side chain and/or an aspartate side chain), and/or a disulfide bond formed from a thiohydroxy group in the peptide or polypeptide (e.g., in a cysteine side chain). In some embodiments, an amino acid residue attached to the linking group is an N-terminal and/or C-terminal residue, for example, any amino acid residue attached via an N-terminal amino group or C-terminal carboxylate group, and/or a terminal lysine, glutamate, aspartate, serine, threonine and/or cysteine residue attached via a side chain thereof.

In some embodiments, an amino acid residue and/or peptide (e.g., from 2 to 20 amino acid residues in length) is added to the N-terminus and/or C-terminus of a peptide or polypeptide sequence of a functional group (according to any of the respective embodiments described herein), and links the aforementioned sequence to a linking group. Examples of such terminal amino acid residues and/or peptides include, without limitation, glycine residues and peptides with a terminal glycine residue, which may be used to attach a linking group to an N-terminus or C-terminus (according to any of the respective embodiments described herein); serine and threonine residues and peptides with a terminal serine or threonine residue, which may be used to attach a linking group to hydroxyl group in a serine or threonine side chain, optionally via an ester bond (according to any of the respective embodiments described herein); and cysteine residues and peptides with a terminal cysteine residue, which may be used to attach a linking group to a peptide via a disulfide bond (according to any of the respective embodiments described herein).

In some embodiments, attachment of a peptide or polypeptide to a linking group via a terminal amino acid residue minimizes interference (e.g., steric interference) with the functionality of the peptide or polypeptide following attachment to the linking group.

In some embodiments, attachment of a peptide or polypeptide to a linking group via a terminal glycine facilitates attachment by minimizing interference (e.g., steric interference) of an amino acid side chain (which glycine lacks) with attachment to the linking group.

Lipids and Liposomes:

As described herein, the liposome according to embodiments comprises at least one bilayer-forming lipid.

Herein, the term "bilayer-forming lipid" encompasses any compound in which a bilayer may form from a pure aqueous solution of the compound, the bilayer comprising two parallel layers of molecules of the compound (referred to as a "lipid").

Typically, the bilayer (e.g., in a liposome according to some of any of the embodiments described herein) comprises relatively polar moieties of the lipid at the two surfaces of the bilayer, which may optionally comprise an interface with the aqueous solution and/or an interface with a solid surface; and relatively hydrophobic moieties of the lipid at the interior of the bilayer, at an interface between the two layers of lipid molecules which form the bilayer.

Examples of bilayer-forming lipids include glycerophospholipids (e.g., a glycerophospholipid according to any of the respective embodiments described herein). It is to be appreciated that the polymeric compound described herein may optionally be a bilayer-forming lipid which can form a bilayer per se or in combination with one or more additional bilayer-forming lipids.

In some embodiments of any one of the embodiments described herein, the bilayer-forming lipid comprises at least one charged group (e.g., one or more negatively charged groups and/or one or more positively charged groups).

In some embodiments, the bilayer-forming lipid is zwitterionic; comprising both (e.g., an equal number of) negatively charged and positively charged groups (e.g., one of each).

In some embodiments of any of the embodiments described herein, a molar ratio of the bilayer-forming lipid (comprised in addition to the polymeric compound) and the polymeric compound in the liposome is in a range of from 5:1 to 5,000:1 (bilayer-forming lipid:polymeric compound), optionally in a range of from 10:1 to 2,500:1, optionally in a range of from 25:1 to 1,000:1, and optionally in a range of from 50:1 to 500:1.

In some embodiments of any of the embodiments described herein, a polymeric moiety in the liposome comprises a lipid moiety represented by the variable X in formula I (according to any of the respective embodiments described herein) which comprises a residue of a bilayer-forming lipid (e.g., a glycerophospholipid) which is comprised by the liposome in addition to the polymeric moiety or which is closely related to a bilayer-forming lipid comprises by the liposome, for example, wherein the lipid moiety comprises a glycerophospholipid residue and the liposome comprises another glycerophospholipid as a bilayer-forming lipid (e.g., optionally wherein fatty acid residues in the glycerophospholipid residue have about the same length as fatty acid residues in the bilayer-forming lipid, and optionally wherein the fatty acid residues in the glycerophospholipid residue are substantially the same as the fatty acid residues in the bilayer-forming lipid).

Without being bound by any particular theory, it is believed that similarity between a lipid moiety of a polymeric moiety and a bilayer-forming lipid facilitates anchorage of the lipid moiety of the polymeric moiety in a liposome comprising the bilayer-forming lipid.

A liposome may optionally comprise a single bilayer (e.g., a unilamellar vesicle) or a plurality of bilayers (e.g., a multilamellar vesicle)—wherein each bilayer optionally independently forms a closed vesicle—comprising, for example, concentric bilayer vesicles and/or a plurality of separate bilayer vesicles encompassed by the same bilayer vesicle.

A liposome according to any of the respective embodiments described herein may be approximately spherical in shape or may have any alternative shape, such as an elongated tube and/or a flattened (e.g., sheet-like) shape.

An average diameter of the liposomes may optionally be in a range of from 20 nm to 1000 nm, optionally from 50 nm to 300 nm.

In some embodiments of any of the embodiments described herein, an average diameter of the liposome is at least 100 nm, for example from 100 to 1000 nm, or from 100 nm to 300 nm. In some embodiments, an average diameter of the liposome is at least 125 nm, for example from 125 to 1000 nm, or from 125 nm to 300 nm. In some embodiments, an average diameter of the liposome is at least 150 nm, for example from 150 to 1000 nm, or from 150 nm to 300 nm. In some embodiments, an average diameter of the liposome is at least 160 nm, for example from 160 to 1000 nm, or from 160 nm to 300 nm. In some embodiments, an average diameter of the liposome is at least 170 nm, for example from 170 to 1000 nm, or from 170 nm to 300 nm.

As exemplified herein, liposome diameters of at least about 100 nm (e.g., about 160-170 nm) are associated with greater retention times in vivo.

Average diameters of liposomes may be determined, for example, by dynamic light scattering measurements according to procedures known in the art (e.g., as described in the examples section herein).

In some embodiments of any of the embodiments described herein relating to a liposome, the liposome further comprises at least one functional moiety or agent (in addition to a therapeutically active agent described herein) bound to a surface of the liposome and/or within a lipid bilayer and/or core of the liposome (e.g., within the liposome bilayer and/or enveloped by the liposome bilayer).

Examples of functional moieties and agents suitable for inclusion in embodiments described herein include, without limitation, a labeling moiety or agent, and/or a targeting moiety or targeting agent (e.g., a targeting moiety or agent on a surface of the liposome).

Examples of a labeling moiety or agent include moieties and compounds which are chromophoric (e.g., absorb visible light), fluorescent, phosphorescent, and/or radioactive. Many such compounds and moieties (and techniques for preparing such moieties) will be known to a skilled person.

A targeting moiety in a liposome according to any of the respective embodiments described herein may optionally be a targeting moiety according to any of the respective embodiments described herein. A targeting moiety in a liposome may be comprised by a polymeric compound according to some embodiments of the invention (according to any of the respective embodiments described herein), the liposome comprising the polymeric compound. Alternatively or additionally, a targeting moiety in a liposome may optionally be comprised by another compound in the liposome, optionally a bilayer-forming lipid (according to any of the respective embodiments described herein) conjugated to a targeting moiety according to any of the respective embodiments described herein.

Herein, a "targeting agent" refers to a compound ("agent") comprising (and optionally consisting essentially of) a targeting moiety according to any of the respective embodiments described herein (e.g., in the context of a targeting moiety comprised by a polymeric compound described herein). Typically, the phrase "targeting agent" is used to refer to a compound other than a polymeric compound comprising a targeting moiety, as described herein.

In some embodiments, a functional moiety (e.g., targeting moiety or labeling moiety) is covalently attached to a liposome. Such attachment may be obtained in some embodiments by using techniques known in the art (e.g., amide bond formation).

Therapeutically Active Agent and Indications:

Herein, the phrase "therapeutically active agent" refers to any agent (e.g., compounds) having a therapeutic effect, as well as to any portion of an agent (e.g., a moiety of a compound) which generates an agent having a therapeutic effect upon release (e.g., upon cleavage of one or more covalent bonds).

A therapeutically active agent incorporated in a liposome and/or on a surface of the liposome may be, for example, be attached by a covalent or non-covalent (e.g., electrostatic and/or hydrophobic) bond to a liposome (e.g., to an exterior surface and/or interior surface of a liposome membrane), incorporated within a liposome membrane (e.g., a lipophilic agent which stably partitions to a lipid phase of the liposome), and/or enveloped within a core of a liposome (e.g., a hydrophilic agent in an aqueous compartment of the liposome).

In some embodiments, a therapeutically active agent is a moiety covalently attached to a liposome (e.g., attached to a lipid so as to form a lipid-derivative comprising the moiety). Such attachment may be obtained in some embodiments by using techniques known in the art (e.g., amide bond formation).

In some embodiments of any of the embodiments described herein, the therapeutically active agent is, for example, an analgesic, an anti-inflammatory agent, an anti-proliferative agent, an anti-microbial agent (including anti-bacterial, anti-mycobacterial, antiviral, anti-fungal, anti-protozoal and/or anti-parasitic agents) and/or a vaccine antigen. In some such embodiments, the therapeutically active agent is an analgesic and/or an anti-inflammatory agent. In some such embodiments, the therapeutically active agent is usable in the treatment osteoarthritis, either alone or in combination with an additional therapeutically active agent.

In some of any of the embodiments described herein, the liposomes of the present embodiments are administered to a subject in need thereof in combination with an additional therapeutically active agent usable in the treatment of an indicated medical condition or a pharmaceutical composition comprising same. The additional therapeutically active agent can be incorporated in liposomes of the present embodiments, in other liposomes, which may have the same or different retention time of the agent, or can be simply mixed with an appropriate, liposome-free carrier.

Examples of suitable analgesics include, without limitation, allylprodine, alphamethylfentanyl, AP-237, bezitramide, butorphanol, buprenorphine, carfentanyl, clonidine, codeine, desmethylprodine, dextromoramide, dexocine, difenoxin, dihydrocodeine, dihydroetorphine, dihydromorphine, diphenoxylate, dipipanone, eluxadoline, ethylmorphine, etorphine, fentanyl, heterocodeine, hydrocone, hydromorphone, ketamine, ketobemidone, lefetamine, levomethadyl (e.g., levomethadyl acetate), levomethorphan, levorphanol, loperamide, meptazinol, methadone, mexiletine, mitragynine, morphine, nalbuphine, ohmefentanyl, oxycodone, oxymorphone, paracetamol, pentazocine, pethidine, phenethylphenylacetoxypiperidine, piritramide, prodine, promedol, propoxyphene, remifentanil, sulfentanil, tapentadol, tilidine, and tramadol.

Non-steroidal anti-inflammatory agents (e.g., a non-steroidal anti-inflammatory agent described herein), as well as steroidal anti-inflammatory agents, may also be used as an analgesic.

Examples of suitable anti-inflammatory agents include, without limitation, alclofenac; alclometasone (e.g., alclometasone dipropionate); algestone (e.g., algestone acetonide); alpha amylase; amcinafal; amcinafide; amfenac (e.g., amfenac sodium); amiprilose (e.g., amiprilose hydrochloride); anakinra; anirolac; anitrazafen; apazone; aspirin; balsalazide disodium; bendazac; benoxaprofen; benzydamine (e.g., benzydamine hydrochloride); bromelains; broperamole; budesonide; carprofen; cicloprofen; cintazone; cliprofen; clobetasol (e.g., clobetasol propionate, clobetasone butyrate); clopirac; cloticasone (cloticasome propionate); cormethasone (cormethasone acetate); cortodoxone; deflazacort; desonide; desoximetasone; dexamethasone (e.g., dexamethasone dipropionate); diclofenac (e.g., diclofenac potassium, diclofenac sodium); diflorasone (e.g., diflorasone diacetate); diflumidone (e.g., diflumidone sodium); diflunisal; difluprednate; diftalone; drocinonide; endrysone; enlimomab; enolicam (e.g., enolicam sodium); epirizole; etodolac; etofenamate; felbinac; fenamole; fenbufen; fenclofenac; fenclorac; fendosal; fenpipalone; fentiazac; flazalone; fluazacort; flufenamic acid; flumizole; flunisolide (e.g., flunisolide acetate); flunixin (e.g., flunixin meglumine); fluocortin (e.g., fluorcortin butyl); fluorometholone (e.g., fluorometholone acetate); fluquazone; flurbiprofen; fluretofen; fluticasone (e.g., fluticasone propionate); furaprofen; furobufen; halcinonide; halobetasol (e.g., halobetasol propionate); halopredone (e.g., halopredone acetate); ibufenac; ibuprofen (e.g., ibuprofen aluminum, ibuprofen piconol); ilonidap; indomethacin (e.g., indomethacin sodium); indoprofen; indoxole; intrazole; isoflupredone (e.g., isoflupredone acetate); isoxepac; isoxicam; ketoprofen; lofemizole (e.g., lofemizole hydrochloride); lomoxicam; loteprednol (e.g., loteprednol etabonate); meclofenamate (e.g., meclofenamate sodium, meclofenamic acid); meclorisone (e.g., meclorisone dibutyrate); mefenamic acid; mesalamine; meseclazone; methylprednisolone (e.g., methylprednisolone suleptanate); momiflumate; nabumetone; naproxen (e.g., naproxen sodium); naproxol; nimazone; olsalazine (e.g., olsalazine sodium); orgotein; orpanoxin; oxaprozin; oxyphenbutazone; paranyline (e.g., paranyline hydrochloride); pentosan polysulfate (e.g., pentosan polysulfate sodium); phenbutazone (e.g., phenbutazone sodium glycerate); pirfenidone; piroxicam (e.g., piroxicam cinnamate, piroxicam olamine); pirprofen; prednazate; prifelone; prodolic acid; proquazone; proxazole (e.g., proxazole citrate); rimexolone; romazarit; salcolex; salicylate (e.g., salicylic acid); salnacedin; salsalate; sanguinarium (e.g., sanguinarium chloride); seclazone; sermetacin; sudoxicam; sulindac; suprofen; talmetacin; talniflumate; talosalate; tebufelone; tenidap (e.g., tenidap sodium); tenoxicam; tesicam; tesimide; tetrydamine; tiopinac; tixocortol (e.g., tixocortol pivalate); tolmetin (e.g., tolmetin sodium); triclonide; triflumidate; zidometacin; and zomepirac (e.g., zomepirac sodium).

Examples of suitable anti-proliferative agents include, without limitation, acivicin; aclarubicin; acodazole (e.g., acodazole hydrochloride); acronine; adriamycin; adozelesin; aldesleukin; altretamine; ambomycin; ametantrone (e.g., ametantrone acetate); aminoglutethimide; amsacrine; anastrozole; anthramycin; asparaginase; asperlin; azacitidine; azetepa; azotomycin; batimastat; benzodepa; bicalutamide; bisantrene (e.g., bisantrene hydrochloride); bisnafide (e.g., bisnafide dimesylate); bizelesin; bleomycin (e.g., bleomycin sulfate); brequinar (e.g., brequinar sodium); bropirimine; busulfan; cactinomycin; calusterone; caracemide; carbetimer; carboplatin; carmustine; carubicin (e.g., carubicin hydrochloride); carzelesin; cedefingol; chlorambucil; cirolemycin; cisplatin; cladribine; combrestatin A-4 phosphate; crisnatol (e.g., crisnatol mesylate); cyclophosphamide; cytarabine; dacarbazine; dactinomycin; daunorubicin (e.g., daunorubicin hydrochloride); decitabine; dexormaplatin; dezaguanine (e.g., dezaguanine mesylate); diaziquone; docetaxel; doxorubicin (e.g., doxorubicin hydrochloride); droloxifene (e.g., droloxifene citrate); dromostanolone (e.g., dromostanolone propionate); duazomycin; edatrexate; eflornithine (e.g., eflornithine hydrochloride); elsamitrucin; enloplatin; enpromate; epipropidine; epirubicin (e.g., epirubicin hydrochloride); erbulozole; esorubicin (e.g., esorubicin hydrochloride); estramustine (e.g., estramustine phosphate sodium); etanidazole; etoposide (e.g., etoposide phosphate); etoprine; fadrozole (e.g., fadrozole hydrochloride); fazarabine; fenretinide; floxuridine; fludarabine (e.g., fludarabine phosphate); fluorouracil; flurocitabine; fosquidone; fostriecin (e.g., fostriecin sodium); gemcitabine (e.g., gemcitabine hydrochloride); hydroxyurea; idarubicin (e.g., idarubicin hydrochloride); ifosfamide; ilmofosine; interferon alfa-2a; interferon alfa-2b; interferon alfa-n1; interferon alfa-n3; interferon beta-Ia; interferon gamma-Ib; iproplatin; irinotecan (e.g., irinotecan hydrochloride); lanreotide (e.g., lanreotide acetate); letrozole; leuprolide (e.g., leuprolide acetate); liarozole (e.g., liarozole hydrochloride); lometrexol (e.g., lometrexol sodium); lomustine; losoxantrone (e.g., losoxantrone hydrochloride); masoprocol; maytansine; mechlorethamine (e.g., mechlorethamine hydrochloride); megestrol (e.g., megestrol acetate); melengestrol (e.g., melengestrol acetate); melphalan; menogaril; mercaptopurine; methotrexate (e.g., methotrexate sodium); metoprine; meturedepa; mitindomide; mitocarcin; mitocromin; mitogillin; mitomalcin; mitomycin; mitosper; mitotane; mitoxantrone (e.g., mitoxantrone hydrochloride); mycophenolic acid; nocodazole; nogalamycin; ombrabulin; ormaplatin; oxisuran; paclitaxel; pegaspargase; peliomycin; pentamustine; peplomycin (e.g., peplomycin sulfate); perfosfamide; pipobroman; piposulfan; piroxantrone (e.g., piroxantrone hydrochloride); plicamycin; plomestane; porfimer (e.g., porfimer sodium); porfiromycin; prednimustine; procarbazine (e.g., procarbazine hydrochloride); puromycin (e.g., puromycin hydrochloride); pyrazofurin; riboprine; rogletimide; safingol (e.g., safingol hydrochloride); semustine; simtrazene; sparfosate (e.g., sparfosate sodium); sparsomycin; spirogermanium (e.g., spirogermanium hydrochloride); spiromustine; spiroplatin; streptonigrin; streptozocin; sulofenur; talisomycin; tecogalan (e.g., tecogalan sodium); tegafur; teloxantrone (e.g., teloxantrone hydrochloride); temoporfin; teniposide; teroxirone; testolactone; thiamiprine; thioguanine; thiotepa; tiazofurin; tirapazamine; topotecan (e.g., topotecan hydrochloride); toremifene (e.g., toremifene citrate); trestolone (e.g., trestolone acetate); triciribine (e.g., triciribine phosphate); trimetrexate (e.g., trimetrexate glucoronate); triptorelin; tubulozole (e.g., tubulozole hydrochloride); uracil mustard; uredepa; vapreotide; verteporfin; vinblastine; vincristine (e.g., vincristine sulfate); vindesine (e.g., vindesine sulfate); vinepidine; vinglycinate; vinleurosine; vinorelbine (e.g., vinorelbine tartrate); vinrosidine; vinzolidine; vorozole; zeniplatin; zinostatin; and zorubicin (e.g., zorubicin hydrochloride). Additional anti-cancer agents include those disclosed in Chapter 52, Antineoplastic Agents (Paul Calabresi and Bruce A. Chabner), and the introduction thereto, 1202-1263, of Goodman and Gilman's "The Pharmacological Basis of Therapeutics", Eighth Edition, 1990, McGraw-Hill, Inc. (Health Professions Division), the contents of which are incorporated herein by reference.

Examples of therapeutically active agents suitable for inclusion in a liposome (e.g., as a molecule or moiety of the agent) according to some embodiments described herein include, without limitation, amphotericin B, cisplatin, cytarabine, daunorubicin, doxorubicin, influenza hemagglutinin and/or neuraminidase, morphine, surfactant protein B, surfactant protein C, verteporfin and vincristine.

Examples of medical conditions treatable by amphotericin B (e.g., via injection and/or infusion of an amphotericin B-comprising liposome according to any of the respective embodiments described herein) include, without limitation, protozoal infections (e.g., leishmaniasis) and fungal infections, such as aspergillosis, blastomycosis, candidiasis, coccidioidomycosis and cryptococcosis.

Inclusion of amphotericin B in a liposome according to any of the respective embodiments described herein may optionally result in reduced toxicity (e.g., reduced renal toxicity) and/or improved pharmacokinetics (e.g., in treating central nervous system infections).

Examples of medical conditions treatable by cytarabine (e.g., via injection and/or infusion of a cytarabine-comprising liposome according to any of the respective embodiments described herein) include, without limitation, cancers, such as leukemia (e.g., acute myeloid leukemia, acute lymphocytic leukemia, chronic myelogenous leukemia), and lymphoma (e.g., non-Hodgkin's lymphoma, lymphomatous meningitis).

Inclusion of cytarabine in a liposome according to any of the respective embodiments described herein may optionally result in enhanced efficacy (e.g., in treating lymphomatous meningitis).

Examples of medical conditions treatable by cisplatin (e.g., via injection and/or infusion of a cisplatin-comprising liposome according to any of the respective embodiments described herein) include, without limitation, cancers, such as bladder cancer, brain tumors, breast cancer, cervical cancer, esophageal cancer, germ cell tumors, head and neck cancer, lung cancer (e.g., small cell lung cancer), mesothelioma, neuroblastoma, ovarian cancer, pancreatic cancer, testicular cancer, and sarcomas.

Examples of medical conditions treatable by daunorubicin (e.g., via injection and/or infusion of a daunorubicin-comprising liposome according to any of the respective embodiments described herein) include, without limitation, cancers, such as leukemia (e.g., acute myeloid leukemia, acute lymphocytic leukemia, chronic myelogenous leukemia), lymphoma (non-Hodgkin's lymphoma), neuroblastoma, and Kaposi's sarcoma (e.g., AIDS-related Kaposi's sarcoma).

Inclusion of daunorubicin in a liposome according to any of the respective embodiments described herein may optionally result in an improved pharmacokinetic profile (e.g., increased concentration) at a site of a lesion (e.g., a Kaposi's sarcoma lesion).

Examples of medical conditions treatable by doxorubicin (e.g., via injection and/or infusion of a doxorubicin-comprising liposome according to any of the respective embodiments described herein) include, without limitation, cancers, such as breast cancer (e.g., in combination with cyclophosphamide), bladder cancer, Kaposi's sarcoma (e.g., AIDS-related Kaposi's sarcoma), leukemia (e.g., acute lymphocytic leukemia), lymphoma (Hodgkin's lymphoma, multiple myeloma), lung cancer, ovarian cancer, soft tissue sarcoma, stomach cancer, and thyroid cancer.

Inclusion of doxorubicin in a liposome according to any of the respective embodiments described herein may optionally result in reduced toxicity (e.g., cardiotoxicity) and/or in an improved pharmacokinetic profile (e.g., increased concentration) at a site of a lesion (e.g., a Kaposi's sarcoma lesion).

Examples of medical conditions treatable by estradiol (e.g., via topical administration of an estradiol-comprising liposome according to any of the respective embodiments described herein) include, without limitation, menopause, hypogonadism, gender dysphoria, infertility, lactation, excessive height (e.g., in adolescent girls), and hormone sensitive cancers (e.g., breast cancer, prostate cancer).

Influenza hemagglutinin and/or neuraminidase may optionally be used to treat (e.g., to prevent) influenza, for example, as an influenza vaccine. The vaccine may optionally be for administration via injection and/or infusion of a liposome (optionally in a form of a virosome) comprising hemagglutinin and/or neuraminidase according to any of the respective embodiments described herein.

Examples of medical conditions treatable by morphine (e.g., via injection and/or infusion of a morphine-comprising liposome according to any of the respective embodiments described herein) include, without limitation, acute and chronic pain (e.g., pain associated with surgery, myocardial infarction and/or labor) and shortness of breath.

Inclusion of morphine in a liposome according to any of the respective embodiments described herein may optionally result in an extended time period (e.g., at least 48 hours) during which a therapeutically effective level of morphine is present in a subject's blood.

Respiratory distress syndrome (e.g., in premature infants) is a non-limiting example of a medical condition treatable by surfactant protein B and/or surfactant protein C, e.g., via pulmonary (e.g., intra-tracheal) administration of a surfactant protein B and/or C-comprising liposome according to any of the respective embodiments described herein).

Examples of medical conditions treatable by verteporfin (e.g., via injection and/or infusion of a verteporfin-comprising liposome according to any of the respective embodiments described herein) include, without limitation, eye disorders, such as abnormal blood vessels in the eye (e.g., associated with wet and/or age-related macular degeneration), pathologic myopia, ocular histoplasmosis, and central serous retinopathy, e.g., in association with photodynamic therapy (e.g., wherein verteporfin is administered prior to laser treatment).

Examples of medical conditions treatable by vincristine (e.g., via injection and/or infusion of a vincristine-comprising liposome according to any of the respective embodiments described herein) include, without limitation, thrombocytopenic purpura (e.g., thrombotic thrombocytopenic purpura or idiopathic thrombocytopenic purpura) and cancers, such as neuroblastoma, nephroblastoma, melanoma, lung cancer (e.g., small cell lung cancer), leukemia (e.g., acute myeloid leukemia, acute lymphocytic leukemia), and lymphoma (e.g., Hodgkin's lymphoma or non-Hodgkin's lymphoma).

Inclusion of vincristine in a liposome according to any of the respective embodiments described herein may optionally result in enhanced efficacy, enhanced entry of vincristine into cells, enhanced plasma concentration and/or circulation lifetime of vincristine, and/or in decreased toxicity (e.g., decreased neurotoxicity).

The skilled person will be readily capable of determining which medical condition(s) may be are treatable by a given therapeutically active agent, as well as which therapeutically active agent(s) may be suitable for treating a given medical condition.

In some embodiments of any of the embodiments described herein, the liposome is for use in the treatment of a proliferative disease or disorder (e.g., cancer), and the therapeutically active agent is an anti-proliferative agent according to any of the respective embodiments described herein.

In some embodiments of any of the embodiments described herein, the liposome is for use in the treatment of an inflammatory disease or disorder (e.g., cancer), and the therapeutically active agent is an analgesic and/or anti-inflammatory agent according to any of the respective embodiments described herein.

In some embodiments of any of the embodiments described herein, the liposome is for use in the treatment of a synovial joint disorder (e.g., via systemic and/or intra-articular administration), optionally an inflammatory synovial joint disorder. Examples of synovial joint disorders treatable according to embodiments of the invention, include, without limitation, arthritis (e.g., osteoarthritis, rheumatoid arthritis and/or psoriatic arthritis), bursitis, carpal tunnel syndrome, fibromyositis, gout, locked joint (e.g., locked joint associated with osteochondritis dissecans and/or synovial osteochondromatosis), tendinitis, traumatic joint injury, and joint injury associated with surgery.

Joint injury associated with surgery may optionally be associated with surgery which directly inflicts damage on an articular surface (e.g., by incision), and/or surgery which damages an articular surface only indirectly. For example, surgery which repairs or otherwise affects tissue in the vicinity of the joint (e.g., ligaments and/or menisci) may be associated with joint injury due to altered mechanics in the joint.

Traumatic joint injury may optionally be injury caused directly by trauma (e.g., inflicted at the time of the trauma) and/or injury caused by previous trauma (e.g., a post-traumatic injury which develops sometime after the trauma).

Formulation and Administration:

The liposomes according to any of the embodiments described herein may be administered to the subject per se, or as part of a pharmaceutical composition.

As used herein a "pharmaceutical composition" refers to a preparation of one or more of the active ingredients described herein with other chemical components such as pharmaceutically acceptable carriers and excipients. The purpose of the pharmaceutical composition is to facilitate administration of the active ingredients (e.g., the therapeutically active agent, with or without the liposome, according to any of the respective embodiments described herein) to the subject.

Herein throughout, the term "pharmaceutically acceptable carrier" refers to a carrier or a diluent that does not cause significant irritation to a subject upon administration in the intended manner, and does not abrogate the activity and properties of the liposomes in the composition (e.g., their ability to reduce a friction coefficient of a surface, as described herein in any one of the respective embodiments). Examples, without limitations, of carriers are: propylene glycol, saline, emulsions and mixtures of organic solvents with water, as well as solid (e.g., powdered) and gaseous carriers.

In some embodiments of any of the embodiments described herein the composition comprises an aqueous carrier which is a pharmaceutically acceptable carrier, for example, wherein the composition is a solution.

Herein, the term "excipient" refers to an inert substance added to the pharmaceutical composition to further facilitate administration of an active ingredient of the present invention or to increase shelf-life stability. Examples, without limitation, of excipients include calcium carbonate, calcium phosphate, various sugars and salts and types of starch, cellulose derivatives, gelatin, vegetable oils, EDTA, EGTA, poly-L-lysine, polyethyleneimine, hexadimethrine bromide, polyethylene glycols and other polyanions or single anions. The pharmaceutical composition may advantageously take the form of foam, aerosol or a gel.

In some embodiments of any of the respective embodiments described herein, the pharmaceutical composition further comprises a water-soluble biopolymer, for example a polypeptide and/or polysaccharide. The polymer may be ionic or non-ionic.

As used herein, the phrase "water-soluble biopolymer" encompasses biopolymers having a solubility of at least 1 gram per liter in an aqueous (e.g., water) environment at pH 7 (at 25° C.).

In some embodiments of any of the embodiments described herein, the water-soluble polymer has a solubility of at least 2 grams per liter (under the abovementioned conditions). In some embodiments, the solubility is at least 5 grams per liter. In some embodiments, the solubility is at least 10 grams per liter. In some embodiments, the solubility is at least 20 grams per liter. In some embodiments, the solubility is at least 50 grams per liter. In some embodiments, the solubility is at least 100 grams per liter.

Examples of suitable non-ionic water-soluble polymers include, without limitation, polyvinylpyrrolidone (also referred to herein interchangeably as povidone and/or PVP) and polyethylene oxide (also referred to herein interchangeably as PEO, PEG and/or polyethylene glycol).

Hyaluronic acid (an ionic polysaccharide) is an exemplary biopolymer.

As exemplified herein, a water-soluble polymer may enhance retention in vivo of a liposome according to some embodiments described herein.

Pharmaceutical compositions (e.g., liposome solutions) for use in accordance with the present invention may be formulated in conventional manner (e.g., by means of conventional mixing or dissolving processes) using one or more pharmaceutically acceptable carriers, optionally comprising excipients and auxiliaries, which facilitate processing of the of the liposomes (and optionally also a water-soluble polymer described herein) into preparations which, can be used pharmaceutically. Proper formulation is dependent upon the route of administration chosen.

Techniques for formulation and administration of compounds may be found in "Remington's Pharmaceutical Sciences" Mack Publishing Co., Easton, PA, latest edition, which is incorporated herein by reference.

The liposomes described herein (optionally with a water-soluble polymer described herein) may be formulated as an aqueous solution per se. Additionally, the solution may be in the form of a suspension and/or emulsions (e.g., the aqueous phase of a suspension or water-in-oil, oil-in-water or water-in-oil-in-oil emulsion), for example, in order to increase the viscosity of the formulation. Aqueous injection suspensions may contain substances, which increase the viscosity of the suspension, such as sodium carboxymethyl cellulose, sorbitol or dextran.

Optionally, the suspension may also contain suitable stabilizers or agents, which increase the solubility of the liposomes described herein (and/or the optional water-soluble polymer described herein), for example, to allow for the preparation of highly concentrated solutions.

In some embodiments, the liposomes described herein (optionally with a water-soluble polymer described herein) may be in powder form for constitution with a suitable vehicle, e.g., sterile, pyrogen-free water, before use.

Suitable routes of administration include any of various suitable systemic and/or local routes of administration.

Suitable routes of administration may, for example, include the inhalation, oral, buccal, rectal, transmucosal, topical, transdermal, intradermal, transnasal, intestinal and/or parenteral routes; the intramuscular, subcutaneous and/or intramedullary injection routes; the intrathecal, direct intraventricular, intravenous, intraperitoneal, intranasal, and/or intraocular injection routes, catheterization with or without angio-balloons; and/or the route of direct injection into a tissue region of the subject.

Parenteral administration according to any of the embodiments described herein may optionally be systemic (e.g., intravenous) and/or local (e.g., intra-articular). The liposomes described herein (optionally with a water-soluble polymer described herein) may be formulated for parenteral administration, e.g., by bolus injection or continuous infusion. The compositions may be suspensions, solutions (e.g., aqueous solution of the active ingredients in water-soluble form) or emulsions in oily or aqueous vehicles, and may contain formulatory agents such as suspending, stabilizing and/or dispersing agents. Suitable lipophilic solvents or vehicles include fatty oils such as sesame oil, or synthetic fatty acids esters such as ethyl oleate, triglycerides or liposomes.

For injection, the liposomes described herein (optionally with a water-soluble polymer described herein) may be formulated in aqueous solutions, preferably in physiologically compatible buffers such as Hank's solution, Ringer's solution, histidine buffer, or physiological saline buffer with or without organic solvents such as propylene glycol, polyethylene glycol.

Formulations for injection may be presented in unit dosage form, e.g., in ampoules or in multi-dose containers with optionally, an added preservative.

For transmucosal administration, penetrants appropriate to the barrier to be permeated are used in the formulation. Such penetrants are generally known in the art.

For oral administration, the pharmaceutical composition can be formulated readily by combining the active ingredients with pharmaceutically acceptable carriers well known in the art. Such carriers enable the pharmaceutical composition to be formulated as tablets, pills, dragees, capsules, liquids, gels, syrups, slurries, suspensions, and the like, for oral ingestion by a patient. Pharmacological preparations for oral use can be made using a solid excipient, optionally grinding the resulting mixture, and processing the mixture of granules, after adding suitable auxiliaries if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carboxymethylcellulose; and/or physiologically acceptable polymers such as polyvinylpyrrolidone (PVP). If desired, disintegrating agents may be added, such as cross-linked polyvinylpyrrolidone, agar, or alginic acid or a salt thereof such as sodium alginate.

Dragee cores are provided with suitable coatings. For this purpose, concentrated sugar solutions may be used which may optionally contain gum arabic, talc, polyvinylpyrrolidone, carbopol gel, polyethylene glycol, titanium dioxide, lacquer solutions and suitable organic solvents or solvent mixtures. Dyestuffs or pigments may be added to the tablets or dragee coatings for identification or to characterize different combinations of active ingredient doses.

Pharmaceutical compositions which can be used orally include push-fit capsules made of gelatin as well as soft, sealed capsules made of gelatin and a plasticizer, such as glycerol or sorbitol. The push-fit capsules may contain the active ingredients in admixture with filler such as lactose, binders such as starches, lubricants such as talc or magnesium stearate and, optionally, stabilizers. In soft capsules, the active ingredients may be dissolved or suspended in suitable liquids, such as fatty oils, liquid paraffin, or liquid polyethylene glycols. In addition, stabilizers may be added.

For buccal administration, the compositions may take the form of tablets or lozenges formulated in conventional manner.

For administration via the inhalation route, the active ingredients for use according to the present invention can be delivered in the form of an aerosol/spray presentation from a pressurized pack or a nebulizer with the use of a suitable propellant, e.g., a fluorochlorohydrocarbon such as dichlorodifluoromethane, trichlorofluoromethane, dichloro-tetrafluoroethane; carbon dioxide; or a volatile hydrocarbon such as butane, propane, isobutane, or mixtures thereof. In the case of a pressurized aerosol, the dosage unit may be determined by providing a valve to deliver a metered amount. Capsules and cartridges of, e.g., gelatin for use in a dispenser may be formulated containing a powder mix of the active ingredients and a suitable powder base such as lactose or starch.

The pharmaceutical composition may also be formulated in rectal compositions such as suppositories or retention enemas, using, e.g., conventional suppository bases such as cocoa butter or other glycerides.

The compositions may be formulated wherein the liposomes are contained in an amount effective to achieve the intended purpose, for example, an amount effective to prevent, alleviate or ameliorate symptoms of a disorder in the subject being treated.

The dosage may vary depending upon the dosage form employed, the route of administration utilized, and the location of administration (e.g., the volume and/or surface of the region contacted with the liposomes).

Determination of a therapeutically effective amount is well within the capability of those skilled in the art (e.g., based on what is known in the art for any given therapeutically active agent), especially in light of the detailed disclosure provided herein.

For any preparation used in the methods of the invention, the therapeutically effective amount or dose can be estimated initially from in vitro and cell culture and in vivo assays. For example, a dose can be formulated in animal models to achieve a desired concentration or titer. Such information can be used to more accurately determine useful doses in humans.

Toxicity and/or therapeutic efficacy of the active ingredients described herein can be determined by standard pharmaceutical procedures in vitro, in cell cultures or experimental animals. The data obtained from these in vitro and cell culture assays and animal studies can be used in formulating a range of dosage for use in human. The dosage may vary depending upon the dosage form employed and the route of administration utilized. The exact formulation, route of administration and dosage can be chosen by the individual physician in view of the patient's condition. (See e.g., Fingl, et al., 1975, in "The Pharmacological Basis of Therapeutics", Ch. 1 p. 1).

Dosage amount and interval may be adjusted individually to provide plasma or brain levels of the active ingredients which are sufficient to achieve the desired therapeutic effect (minimal effective concentration, MEC). The MEC will vary for each preparation, but can be estimated from in vitro data. Dosages necessary to achieve the MEC will depend on individual characteristics and route of administration. Detection assays can be used to determine plasma concentrations.

The amount of a composition to be administered will, of course, be dependent on the subject being treated, the severity of the affliction, the manner of administration, the judgment of the prescribing physician, etc.

Depending on the severity and responsiveness of the condition to be treated, dosing can be of a single or a plurality of administrations, with course of treatment lasting from several days to several weeks or until cure is effected or diminution of the disease state is achieved.

Compositions (e.g., liposome solutions) according to embodiments of the present invention may, if desired, be presented in a pack or dispenser device, such as an FDA (the U.S. Food and Drug Administration) approved kit, which may contain one or more unit dosage forms containing the active ingredient(s) (e.g., liposomes described herein). The pack may, for example, comprise metal or plastic foil, such as, but not limited to a blister pack. The pack or dispenser device may be accompanied by instructions for administration. The pack or dispenser may also be accompanied by a notice associated with the container in a form prescribed by a governmental agency regulating the manufacture, use or sale of pharmaceuticals, which notice is reflective of approval by the agency of the form of the compositions for human or veterinary administration. Such notice, for example, may be of labeling approved by the U.S. Food and Drug Administration for prescription drugs or of an approved product insert. Compositions comprising liposomes (optionally with a water-soluble polymer described herein), as described herein in any one of the respective embodiments, formulated in a pharmaceutically acceptable carrier may also be prepared, placed in an appropriate container, and labeled for treatment of an indicated condition or diagnosis, as is detailed herein.

Additional Definitions

Herein, the term "hydrocarbon" describes an organic moiety that includes, as its basic skeleton, a chain of carbon atoms, substituted mainly by hydrogen atoms. The hydrocarbon can be saturated or non-saturated, be comprised of aliphatic, alicyclic or aromatic moieties, and can optionally be substituted by one or more substituents (other than hydrogen). A substituted hydrocarbon may have one or more substituents, whereby each substituent group can independently be, for example, cycloalkyl, alkenyl, alkynyl, aryl, heteroaryl, heteroalicyclic, amine, halide, sulfonate, sulfoxide, phosphonate, hydroxy, alkoxy, aryloxy, thiohydroxy, thioalkoxy, thioaryloxy, oxo, cyano, nitro, azo, azide, sulfonamide, carboxy, thiocarbamate, urea, thiourea, carbamate, amide, and hydrazine. The hydrocarbon can be an end group or a linking group, as these terms are defined herein. The hydrocarbon moiety is optionally interrupted by one or more heteroatoms, including, without limitation, one or more oxygen, nitrogen and/or sulfur atoms. In some embodiments of any of the embodiments described herein relating to a hydrocarbon, the hydrocarbon is not interrupted by any heteroatoms.

Preferably, the hydrocarbon moiety has 1 to 20 carbon atoms. Whenever a numerical range; e.g., "1 to 20", is stated herein, it implies that the group, in this case the alkyl group, may contain 1 carbon atom, 2 carbon atoms, 3 carbon atoms, etc., up to and including 20 carbon atoms.

Herein, the term "alkyl" describes a saturated aliphatic hydrocarbon end group, as defined herein, including straight chain and branched chain groups. Preferably, the alkyl group has 1 to 20 carbon atoms. More preferably, the alkyl is a medium size alkyl having 1 to 10 carbon atoms. Most preferably, unless otherwise indicated, the alkyl is a lower alkyl having 1 to 4 carbon atoms. The alkyl group may be substituted or non-substituted. Substituted alkyl may have one or more substituents, whereby each substituent group can independently be, for example, cycloalkyl, alkenyl, alkynyl, aryl, heteroaryl, heteroalicyclic, amine, halide, sulfonate, sulfoxide, phosphonate, hydroxy, alkoxy, aryloxy, thiohydroxy, thioalkoxy, thioaryloxy, cyano, nitro, azo, azide, sulfonamide, carboxy, thiocarbamate, urea, thiourea, carbamate, amide, and hydrazine.

The term "alkylene" describes a saturated aliphatic hydrocarbon linking group, as this term is defined herein, which differs from an alkyl group, as defined herein, only in that alkylene is a linking group rather than an end group.

Herein, the term "alkenyl" describes an unsaturated aliphatic hydrocarbon end group which comprises at least one carbon-carbon double bond, including straight chain and branched chain groups. Preferably, the alkenyl group has 2 to 20 carbon atoms. More preferably, the alkenyl is a medium size alkenyl having 2 to 10 carbon atoms. Most preferably, unless otherwise indicated, the alkenyl is a lower alkenyl having 2 to 4 carbon atoms. The alkenyl group may be substituted or non-substituted. Substituted alkenyl may have one or more substituents, whereby each substituent group can independently be, for example, cycloalkyl, alkynyl, aryl, heteroaryl, heteroalicyclic, amine, halide, sulfonate, sulfoxide, phosphonate, hydroxy, alkoxy, aryloxy, thiohydroxy, thioalkoxy, thioaryloxy, cyano, nitro, azo, azide, sulfonamide, carboxy, thiocarbamate, urea, thiourea, carbamate, amide, and hydrazine.

Herein, the term "alkynyl" describes an unsaturated aliphatic hydrocarbon end group which comprises at least one carbon-carbon triple bond, including straight chain and branched chain groups. Preferably, the alkynyl group has 2 to 20 carbon atoms. More preferably, the alkynyl is a medium size alkynyl having 2 to 10 carbon atoms. Most preferably, unless otherwise indicated, the alkynyl is a lower alkynyl having 2 to 4 carbon atoms. The alkynyl group may be substituted or non-substituted. Substituted alkynyl may have one or more substituents, whereby each substituent group can independently be, for example, cycloalkyl, alkenyl, aryl, heteroaryl, heteroalicyclic, amine, halide, sulfonate, sulfoxide, phosphonate, hydroxy, alkoxy, aryloxy, thiohydroxy, thioalkoxy, thioaryloxy, cyano, nitro, azo, azide, sulfonamide, carboxy, thiocarbamate, urea, thiourea, carbamate, amide, and hydrazine.

The term "cycloalkyl" describes an all-carbon monocyclic or fused ring (i.e., rings which share an adjacent pair of carbon atoms) group where one or more of the rings does not have a completely conjugated pi-electron system. The cycloalkyl group may be substituted or non-substituted. Substituted cycloalkyl may have one or more substituents, whereby each substituent group can independently be, for example, alkyl, alkenyl, alkynyl, cycloalkyl, aryl, heteroaryl, heteroalicyclic, amine, halide, sulfonate, sulfoxide, phosphonate, hydroxy, alkoxy, aryloxy, thiohydroxy, thioalkoxy, thioaryloxy, cyano, nitro, azo, azide, sulfonamide, carboxy, thiocarbamate, urea, thiourea, carbamate, amide, and hydrazine. The cycloalkyl group can be an end group, as this phrase is defined herein, wherein it is attached to a single adjacent atom, or a linking group, as this phrase is defined herein, connecting two or more moieties.

The term "aryl" describes an all-carbon monocyclic or fused-ring polycyclic (i.e., rings which share adjacent pairs of carbon atoms) end group (as this term is defined herein) having a completely conjugated pi-electron system. The aryl group may be substituted or non-substituted. Substituted aryl may have one or more substituents, whereby each substituent group can independently be, for example, alkyl, alkenyl, alkynyl, cycloalkyl, aryl, heteroaryl, heteroalicyclic, amine, halide, sulfonate, sulfoxide, phosphonate, hydroxy, alkoxy, aryloxy, thiohydroxy, thioalkoxy, thioaryloxy, cyano, nitro, azo, azide, sulfonamide, carboxy, thiocarbamate, urea, thiourea, carbamate, amide, and hydrazine. Phenyl and naphthyl are representative aryl end groups.

The term "heteroaryl" describes a monocyclic or fused ring (i.e., rings which share an adjacent pair of atoms) group having in the ring(s) one or more atoms, such as, for example, nitrogen, oxygen and sulfur and, in addition, having a completely conjugated pi-electron system. Examples, without limitation, of heteroaryl groups include pyrrole, furan, thiophene, imidazole, oxazole, thiazole, pyrazole, pyridine, pyrimidine, quinoline, isoquinoline and purine. The heteroaryl group may be substituted or non-substituted. Substituted heteroaryl may have one or more substituents, whereby each substituent group can independently be, for example, alkyl, alkenyl, alkynyl, cycloalkyl, aryl, heteroaryl, heteroalicyclic, amine, halide, sulfonate, sulfoxide, phosphonate, hydroxy, alkoxy, aryloxy, thiohydroxy, thioalkoxy, thioaryloxy, cyano, nitro, azo, azide, sulfonamide, carboxy, thiocarbamate, urea, thiourea, carbamate, amide, and hydrazine. The heteroaryl group can be an end group, as this phrase is defined herein, where it is attached to a single adjacent atom, or a linking group, as this phrase is defined herein, connecting two or more moieties. Representative examples are pyridine, pyrrole, oxazole, indole, purine and the like.

The term "arylene" describes a monocyclic or fused-ring polycyclic linking group, as this term is defined herein, and encompasses linking groups which differ from an aryl or heteroaryl group, as these groups are defined herein, only in that arylene is a linking group rather than an end group.

The term "heteroalicyclic" describes a monocyclic or fused ring group having in the ring(s) one or more atoms such as nitrogen, oxygen and sulfur. The rings may also have one or more double bonds. However, the rings do not have a completely conjugated pi-electron system. The heteroalicyclic may be substituted or non-substituted. Substituted heteroalicyclic may have one or more substituents, whereby each substituent group can independently be, for example, alkyl, alkenyl, alkynyl, cycloalkyl, aryl, heteroaryl, heteroalicyclic, amine, halide, sulfonate, sulfoxide, phosphonate, hydroxy, alkoxy, aryloxy, thiohydroxy, thioalkoxy, thioaryloxy, cyano, nitro, azo, azide, sulfonamide, carboxy, thiocarbamate, urea, thiourea, carbamate, amide, and hydrazine. The heteroalicyclic group can be an end group, as this phrase is defined herein, where it is attached to a single adjacent atom, or a linking group, as this phrase is defined herein, connecting two or more moieties. Representative examples are piperidine, piperazine, tetrahydrofuran, tetrahydropyran, morpholine and the like.

As used herein, the terms "amine" and "amino" describe both a —NRxRy end group and a —NRx- linking group, wherein Rx and Ry are each independently hydrogen, alkyl, cycloalkyl, aryl, heteroaryl or heteroalicyclic, as these terms are defined herein. When Rx or Ry is heteroaryl or heteroalicyclic, the amine nitrogen atom is bound to a carbon atom of the heteroaryl or heteroalicyclic ring. A carbon atom attached to the nitrogen atom of an amine is not substituted by =O or =S, and in some embodiments, is not substituted by any heteroatom.

The amine group can therefore be a primary amine, where both Rx and Ry are hydrogen, a secondary amine, where Rx is hydrogen and Ry is alkyl, cycloalkyl, aryl, heteroaryl or heteroalicyclic, or a tertiary amine, where each of Rx and Ry is independently alkyl, cycloalkyl, aryl, heteroaryl or heteroalicyclic.

The terms "hydroxy" and "hydroxyl" describe a —OH group.

The term "alkoxy" describes both an —O-alkyl and an —O-cycloalkyl end group, or —O— alkylene or —O-cycloalkyl linking group, as defined herein.

The term "aryloxy" describes both an —O-aryl and an —O-heteroaryl end group, or an —O-arylene- linking group, as defined herein.

The term "thiohydroxy" describes a —SH group.

The term "thioalkoxy" describes both an —S-alkyl and an —S-cycloalkyl end group, or —S— alkylene or —S-cycloalkyl linking group, as defined herein.

The term "thioaryloxy" describes both an —S-aryl and an —S-heteroaryl end group, or an —S-arylene- linking group, as defined herein.

The terms "cyano" and "nitrile" describe a —C≡N group.

The term "nitro" describes an $—NO_2$ group.

The term "oxo" describes a =O group.

The term "azide" describes an $—N{=}N^+{=}N^-$ group.

The term "azo" describes an —N=N—Rx end group or —N=N= linking group, with Rx as defined herein.

The terms "halide" and "halo" refer to fluorine, chlorine, bromine or iodine.

The term "phosphate" refers to a —O—P(=O)(ORx)-$OR_Y$ end group, or to a —O—P(=O)(ORx)—O— linking group, where Rx and $R_Y$ are as defined herein.

The terms "phosphonyl" and "phosphonate" refer to an —P(=O)(ORx)-$OR_Y$ end group, or to a —P(=O)(ORx)—O— linking group, where Rx and $R_Y$ are as defined herein. The term "phosphinyl" refers to a —PRx$R_Y$ group, where Rx and $R_Y$ are as defined hereinabove.

The term "sulfoxide" or "sulfinyl" describes a —S(=O)—Rx end group or —S(=O)— linking group, where Rx is as defined herein.

The terms "sulfonate" and "sulfonyl" describe a $—S(=O)_2—$Rx end group or $—S(=O)_2—$ linking group, where Rx is as defined herein.

The terms "sulfonamide" and "sulfonamido", as used herein, encompass both S-sulfonamide and N-sulfonamide end groups, and a $—S(=O)_2—$NRx- linking group.

The term "S-sulfonamide" describes a $—S(=O)_2—$NRx$R_Y$ end group, with Rx and $R_Y$ as defined herein.

The term "N-sulfonamide" describes an $RxS(=O)_2—$$NR_Y—$ end group, where Rx and $R_Y$ are as defined herein.

The term "carbonyl" as used herein, describes a —C(=O)—Rx end group or —C(=O)— linking group, with Rx as defined herein.

The term "acyl" as used herein, describes a —C(=O)—Rx end group, with Rx as defined herein.

The term "thiocarbonyl" as used herein, describes a —C(=S)—Rx end group or —C(=S)— linking group, with Rx as defined herein.

The terms "carboxy" and "carboxyl", as used herein, encompasses both C-carboxy and O-carboxy end groups, and a —C(=O)—O— linking group.

The term "C-carboxy" describes a —C(=O)—ORx end group, where Rx is as defined herein.

The term "O-carboxy" describes a —OC(=O)—Rx end group, where Rx is as defined herein.

The term "urea" describes a —NRxC(=O)—NRyRw end group or —NRxC(=O)—NRy- linking group, where Rx and Ry are as defined herein and Rw is as defined herein for Rx and Ry.

The term "thiourea" describes a —NRx-C(=S)—NRyRw end group or a —NRx-C(=S)—NRy- linking group, with Rx, Ry and Ry as defined herein.

The terms "amide" and "amido", as used herein, encompasses both C-amide and N-amide end groups, and a —C(=O)—NRx- linking group.

The term "C-amide" describes a —C(=O)—NRxRy end group, where Rx and Ry are as defined herein.

The term "N-amide" describes a RxC(=O)—NRy- end group, where Rx and Ry are as defined herein.

The term "carbamyl" or "carbamate", as used herein, encompasses N-carbamate and O-carbamate end groups, and a —OC(=O)—NRx- linking group.

The term "N-carbamate" describes a RyOC(=O)—NRx- end group, with Rx and Ry as defined herein.

The term "O-carbamate" describes an —OC(=O)—NRxRy end group, with Rx and Ry as defined herein.

The term "thiocarbamyl" or "thiocarbamate", as used herein, encompasses O-thiocarbamate, S-thiocarbamate and N-thiocarbamate end groups, and a —OC(=S)—NRx- or —SC(=O)—NRx- linking group.

The terms "O-thiocarbamate" and "O-thiocarbamyl" describe a —OC(=S)—NRxRy end group, with Rx and Ry as defined herein.

The terms "S-thiocarbamate" and "S-thiocarbamyl" describe a —SC(=O)—NRxRy end group, with Rx and Ry as defined herein.

The terms "N-thiocarbamate" and "N-thiocarbamyl" describe a RyOC(=S)NRx- or RySC(=O)NRx- end group, with Rx and Ry as defined herein.

The term "guanidine" describes a —RxNC(=N)—NRyRw end group or —RxNC(=N)—NRy- linking group, where Rx, Ry and Rw are as defined herein.

The term "hydrazine", as used herein, describes a —NRx-NRyRw end group or —NRx-NRy- linking group, with Rx, Ry, and Rw as defined herein.

As used herein the term "about" refers to ±10%, and optionally ±5%.

The terms "comprises", "comprising", "includes", "including", "having" and their conjugates mean "including but not limited to".

The term "consisting of" means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular form "a", "an" and "the" include plural references unless the context clearly dictates otherwise. For example, the term "a compound" or "at least one compound" may include a plurality of compounds, including mixtures thereof.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral)

within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

As used herein, the term "treating" includes abrogating, substantially inhibiting, slowing or reversing the progression of a condition, substantially ameliorating clinical or aesthetical symptoms of a condition or substantially preventing the appearance of clinical or aesthetical symptoms of a condition.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub-combination or as suitable in any other described embodiment of the invention. Certain features described in the context of various embodiments are not to be considered essential features of those embodiments, unless the embodiment is inoperative without those elements.

Various embodiments and aspects of the present invention as delineated hereinabove and as claimed in the claims section below find experimental support in the following examples.

EXAMPLES

Reference is now made to the following examples, which together with the above descriptions illustrate some embodiments of the invention in a non-limiting fashion.

Materials and Methods

Materials

2-Bromoisobutyryl bromide was obtained from Sigma-Aldrich.

Chloroform was obtained from Sigma-Aldrich.

CuBr was obtained from Sigma-Aldrich.

DiR (1,1'-dioctadecyl-3,3,3',3'-tetramethylindotricarbocyanine iodide) was obtained from Molecular Probes.

Distearoylphosphatidylethanolamine (DSPE) was obtained from Avanti Polar Lipids.

Distearoylphosphatidylethanolamine-polyethylene glycol (DSPE-PEG, with PEG Mw of 2000 Da (DSPE-PEG 2000) or 550 Da (DSPE-PEG 550)) was obtained from Avanti.

Hyaluronic acid (2500 had) was obtained from Creative PEGWorks.

Hydrogenated soy phosphatidylcholine (HSPC) was obtained from Lipoid GmbH.

Methanol was obtained from Bio-Lab.

N,N,N',N",N"-pentamethyldiethylenetriamine (PMDETA) was obtained from Sigma-Aldrich.

O-(2-methacryloyloxyethyl)phosphorylcholine (MPC) was obtained from Biocompatible Corporation (UK).

Phosphate buffer saline (PBS) was obtained from Sigma-Aldrich.

Water was purified using a Barnstead NanoPure system to 18.2 MΩ cm resistance with total organic content levels of <ca.1 ppb.

Synthesis of DSPE-PMPC:

A phospholipid with a polymerized phosphocholine derivative was prepared from the phospholipid DSPE (distearoylphosphatidylethanolamine) and the phosphocholine derivative MPC (O-(2-methacryloyloxyethyl)phosphorylcholine), as depicted schematically in Scheme 1, using procedures described in International Patent Application IL2016/051372. Briefly, DSPE was reacted with 2-bromoisobutyryl bromide in order to obtain a free radical initiator (DSPE-Br), which was then used in atom transfer radical polymerization with MPC (O-(2-methacryloyloxyethyl)phosphorylcholine) in the presence of CuBr and PMDETA (N,N,N',N",N"-pentamethyldiethylenetriamine), at 60° C. The obtained DSPE-PMPC was purified by dialysis, and had a pMPC moiety with a Mw of about 2 kDa, as determined by $^{1}$H-NMR spectroscopy.

Scheme 1

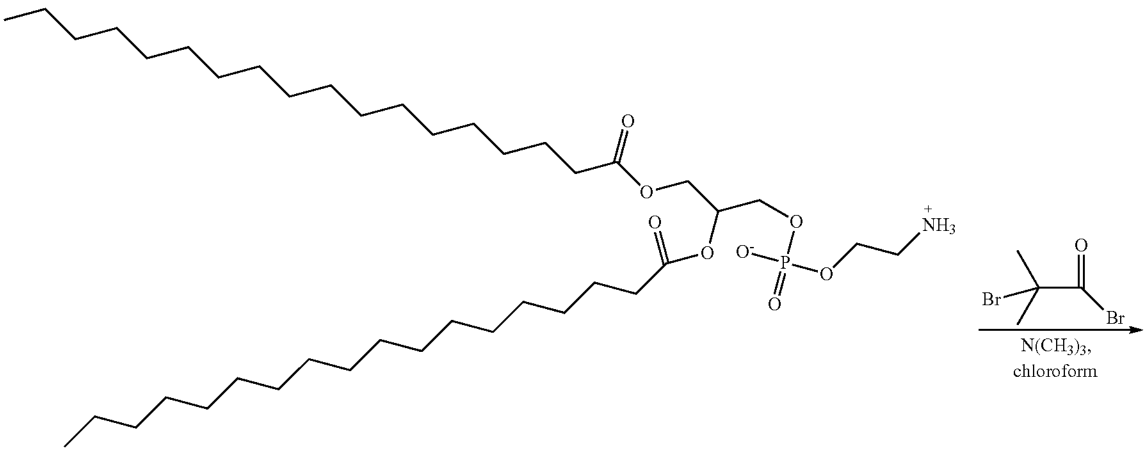

DSPE

-continued

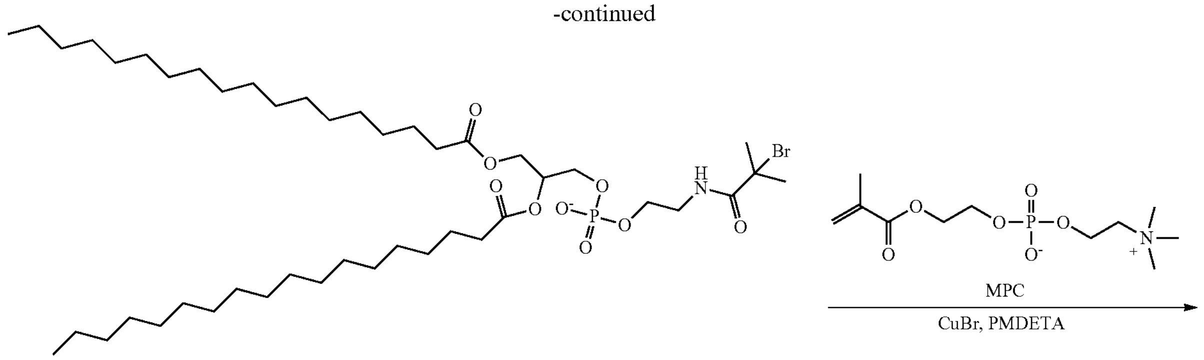

DSPE-Br

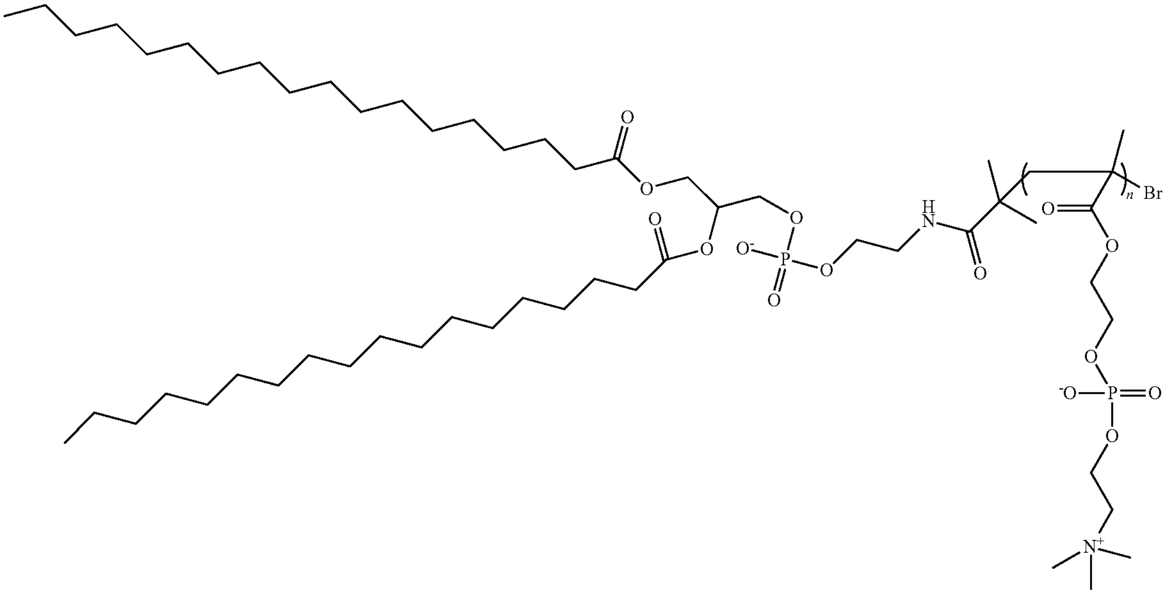

DSPE-pMPC

Liposome Preparation:

To prepare liposomes, DSPE-PMPC (prepared as described hereinabove) and HSPC at molar ratio of 2:98 (DSPE-PMPC:HSPC) were dissolved in methanol and chloroform (2 ml, 1:1 v/v). The organic solvent was then dried by nitrogen overnight to form a dry film. Multilamellar vesicles (MLV) were then prepared by hydrating the lipids at least 5° C. above the lipid melting point, followed by sonication, in PBS (phosphate buffer saline). In order to prepare PEGylated liposomes, the aforementioned procedure was applied on the following mixtures: DSPE-PEG 2000 and HSPC and DSPE-PEG 550 and HSPC, both at molar ratio of 2:98, to form MLVs. The organic solvents that were used are chloroform for the HSPC, and methanol for the DSPE-PMPC and DSPE-PEG.

MLVs were downsized to form large unilamellar vesicles (LUV), by stepwise extrusion through polycarbonate membranes, using a Lipex 10 ml extruder system (Northern Lipids, Canada). In some cases, MLVs were downsized to form small unilamellar vesicles (SUV), by stepwise extrusion through polycarbonate membranes starting with a 400-nm and ending with 50-nm pore-size membrane, using a Lipex 10 ml extruder system (Northern Lipids, Canada).

Dynamic light scattering measurements (DLS) revealed an average diameter of about 170 nm for LUVs and about 80 nm for SUVs.

Animal Experiments:

All animal experiments were performed according to the National Institute of Health (NIH) guidelines for animal research under a protocol approved by the Institutional Animal Care and Use Committee (IACUC) at the Weizmann Institute of Science, Israel.

Example 1

Safety of Intra-Articular Injection of pMPC-Containing Liposomes

In order to assess the safety of pMPC-containing liposomes, mice received an intra-articular (IA) injection of pMPC-containing liposomes (prepared as described in the Materials and Methods section hereinabove) at a 3-fold higher dosage than the concentration used in the following studies (30 mM vs. 11 mM). The negative control was a group of mice which received an IA injection of saline, and the positive control was a group of mice which received an IA injection of hyaluronic acid (HA). Each group contained 6 mice which received an injection into their right knee joint cavity. At 14 days and 28 days post-injection, 3 mice were sacrificed at each time point, and were examined by an expert histopathologist (at the Weizmann Institute Veterinary Services Dept.) by both gross pathological evaluation of the tissue and by examination of H&E (hematoxylin & eosin) histology. Each injected knee was compared to both negative and positive controls, and relative to the left knee (which was not injected).

All results were within normal limits (WNL), indicating that the pMPC-containing liposomes were safe when injected.

Example 2

Retention of pMPC-Containing Liposomes Following Intra-Articular Injection

Mice received an intra-articular (IA) injection of pMPC-containing liposomes (prepared as described in the Materials and Methods section hereinabove), using procedures described in Example 1, and were monitored using a near infra-red camera. In order to detect injected substances in living tissue, all injected substances were functionalized with DiR (1,1'-dioctadecyl-3,3,3',3'-tetramethylindotricarbocyanine iodide), a lipophilic fluorescent dye, so as to fluoresce at a wavelength of about 755 nm. A representative example of detection of an injected substance in living tissue is shown in FIG. 1.

Figure 2A:
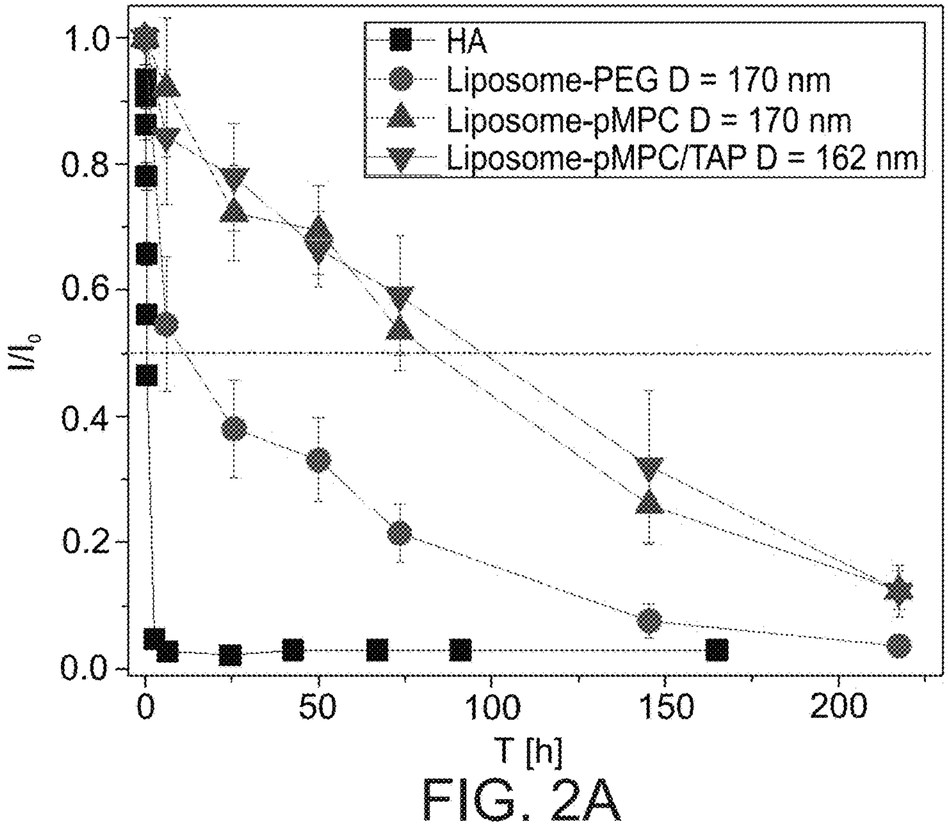
FIGS. 2A-2D present graphs showing fluorescence signals in mice as a function of time after intra-articular injection of fluorescent-labeled hyaluronic acid (HA.
Figure 2B:
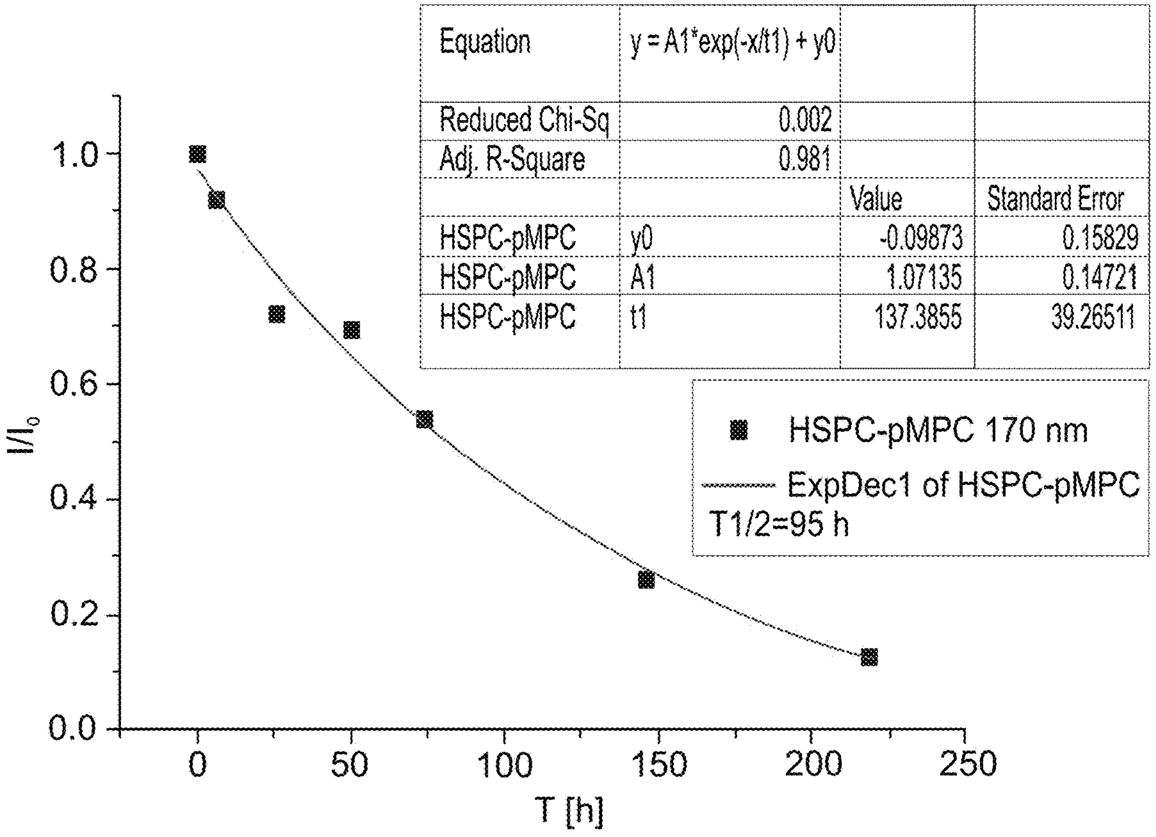
Figure 2C:
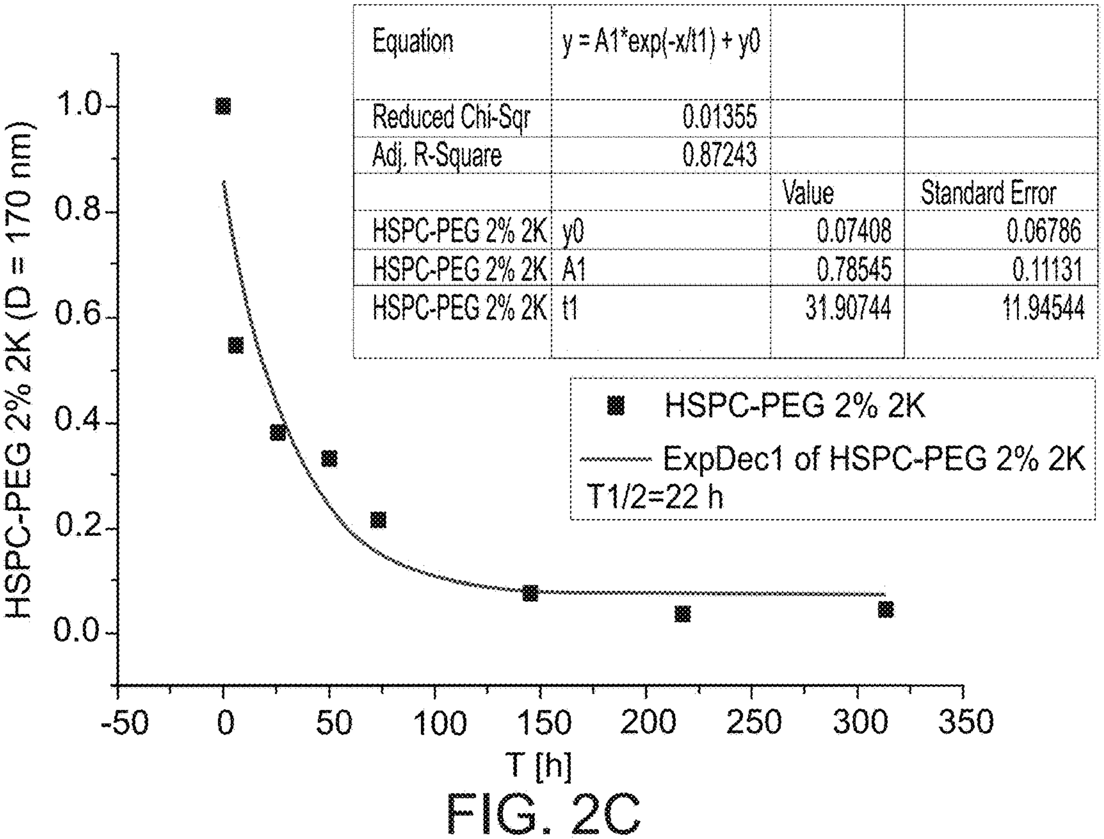

As shown in FIGS. 2A-2C, exemplary pMPC-stabilized liposomes (170 nm in diameter) exhibited a half-life of about 95 hours (FIGS. 2A and 2B), which was considerably greater than the half-life of either hyaluronic acid (less than 1 hour; FIG. 2A) or the half-life of PEGylated liposomes (with 2000 Da PEG) of the same size, which was about 12 hours as determined by visual observation of plotted data (FIG. 2A) and about 22 hours as determined by an exponential fit (FIG. 2C).

The effect of liposome size was further assessed by determining the retention half-lives of exemplary pMPC-stabilized or PEGylated HSPC liposomes with average diameters in a range of from about 140-150 nm to about 170 nm. The pMPC-stabilized liposomes with an average diameter of more than 150 nm exhibited a half-life between 70 and 95 hours, which was approximately twice the half-life of pMPC-stabilized liposomes with an average diameter of about 140-150 nm; whereas the half-life of the PEGylated liposomes did not exhibit such size dependence, and was lower than that of pMPC-stabilized liposomes throughout the abovementioned size range (data not shown).

Figure 3:
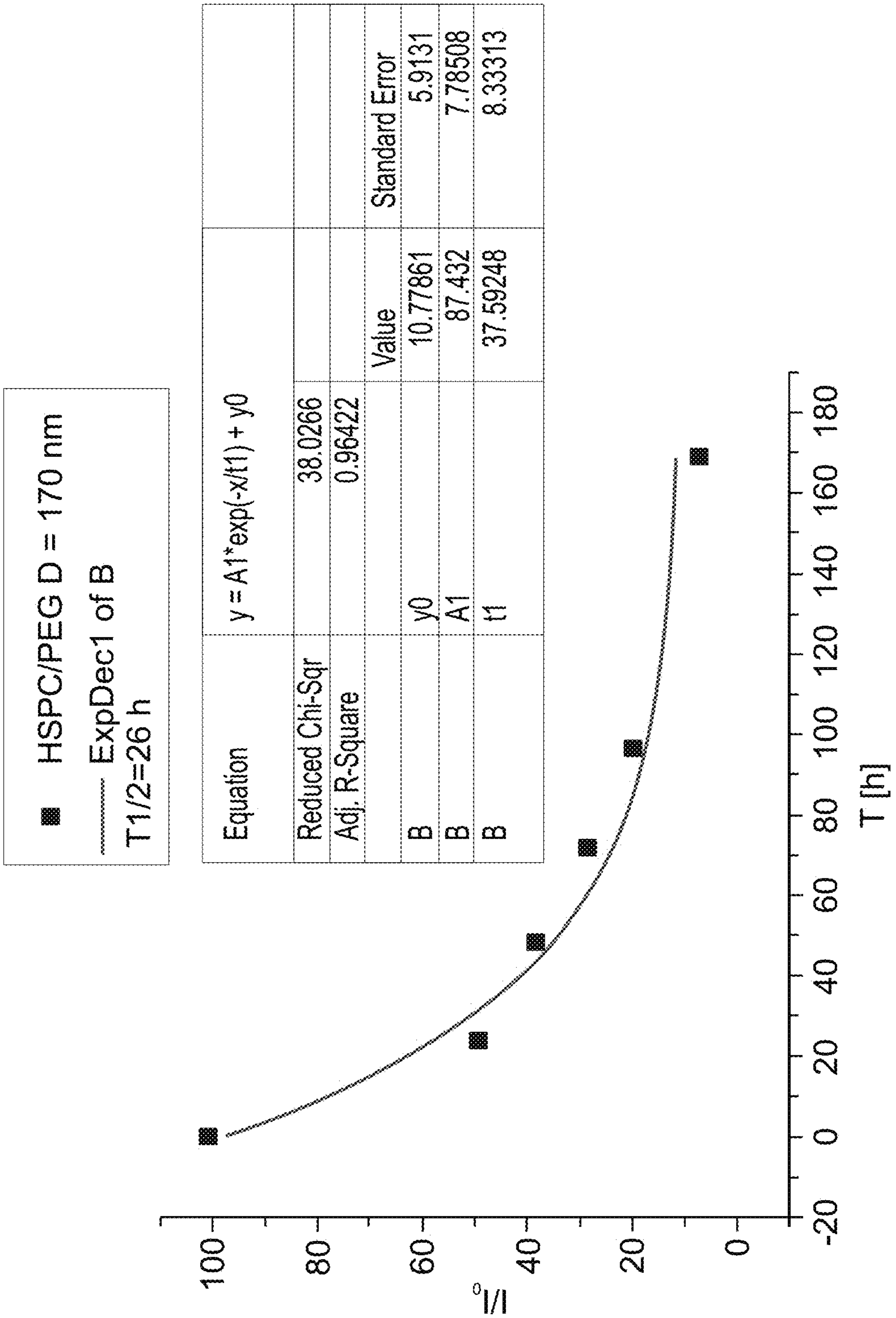
FIG. 3 presents a graph showing fluorescence signals in a mouse as a function of time after intra-articular injection of fluorescent-labeled hydrogenated soy phosphatidylcholine (HSPC) liposomes with 2 kDa PEG moieties, along with exponential fit to the data (from which a calculated half-life of 26 hours was derived); mean liposome diameter was 170 nm.

As shown in FIG. 3, the half-life of PEGylated liposomes (with 2000 Da PEG) was about 20 hours as determined by visual observation of plotted data and about 26 hours as determined by an exponential fit, similar to the results presented in FIGS. 2A and 2C.

These results indicate that pMPC-stabilization of liposomes enhances retention in vivo to a considerably greater extent (e.g., about 4-fold to 8-fold, with enhancement being strongest for liposomes with an average diameter of at least 150 nm) than does PEGylation of liposomes, which has been heretofore considered in the art to be the most effective technique for enhancing liposome retention.

Figure 4:
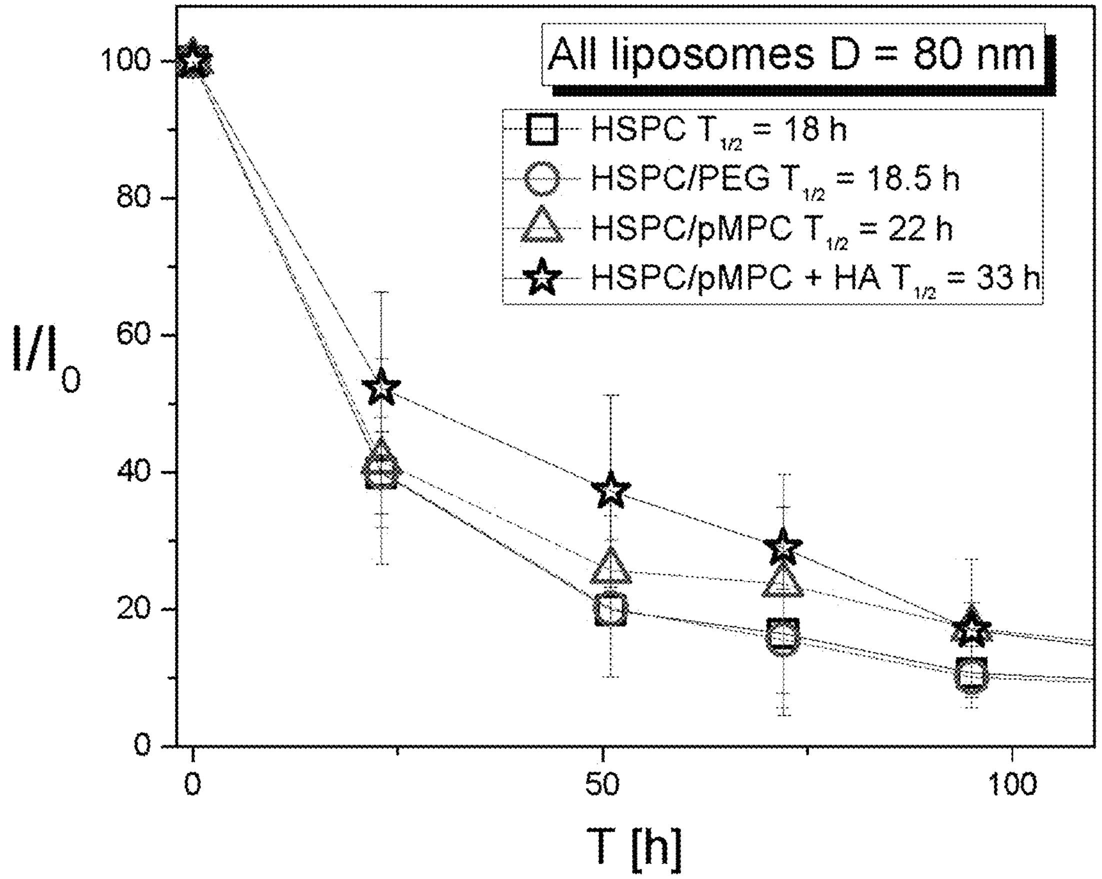
FIG. 4 presents a graph showing fluorescence signals in mice as a function of time after intra-articular injection of fluorescent-labeled liposomes with a mean diameter of 80 nm, comprising hydrogenated soy phosphatidylcholine (HSPC) or HSPC with 2 kDa PEG moieties or 2 kDa pMPC moieties, alone or in combination with hyaluronic acid (HA); calculated half-lives ($T_{1/2}$) are also presented; mean liposome diameter was 80 nm.

As shown in FIG. 4, decreasing the liposome diameter to 80 nm (small unilamellar vesicles) results in considerably shorter half-time values of about 20 hours for all liposome types. However, as further shown therein, addition of 1 mg/ml of HA to the 80 nm pMPC-stabilized liposomes resulted in a 50% increase in the retention time.

The above results relate to liposomes stabilized by a polymer (pMPC or PEG) having a molecular weight of 2000 Da. As the MPC monomeric unit has a higher molecular weight than that of ethylene glycol, the total length of the pMPC chain is much shorter than a PEG chain of the same molecular weight. In order to assess whether the enhanced retention time associated with pMPC is due to its shorter length, PEGylated liposomes were prepared with a molecular weight of only 550 Da (which has a degree of polymerization which is roughly equal to that of the 2000 Da pMPC).

Figure 5:
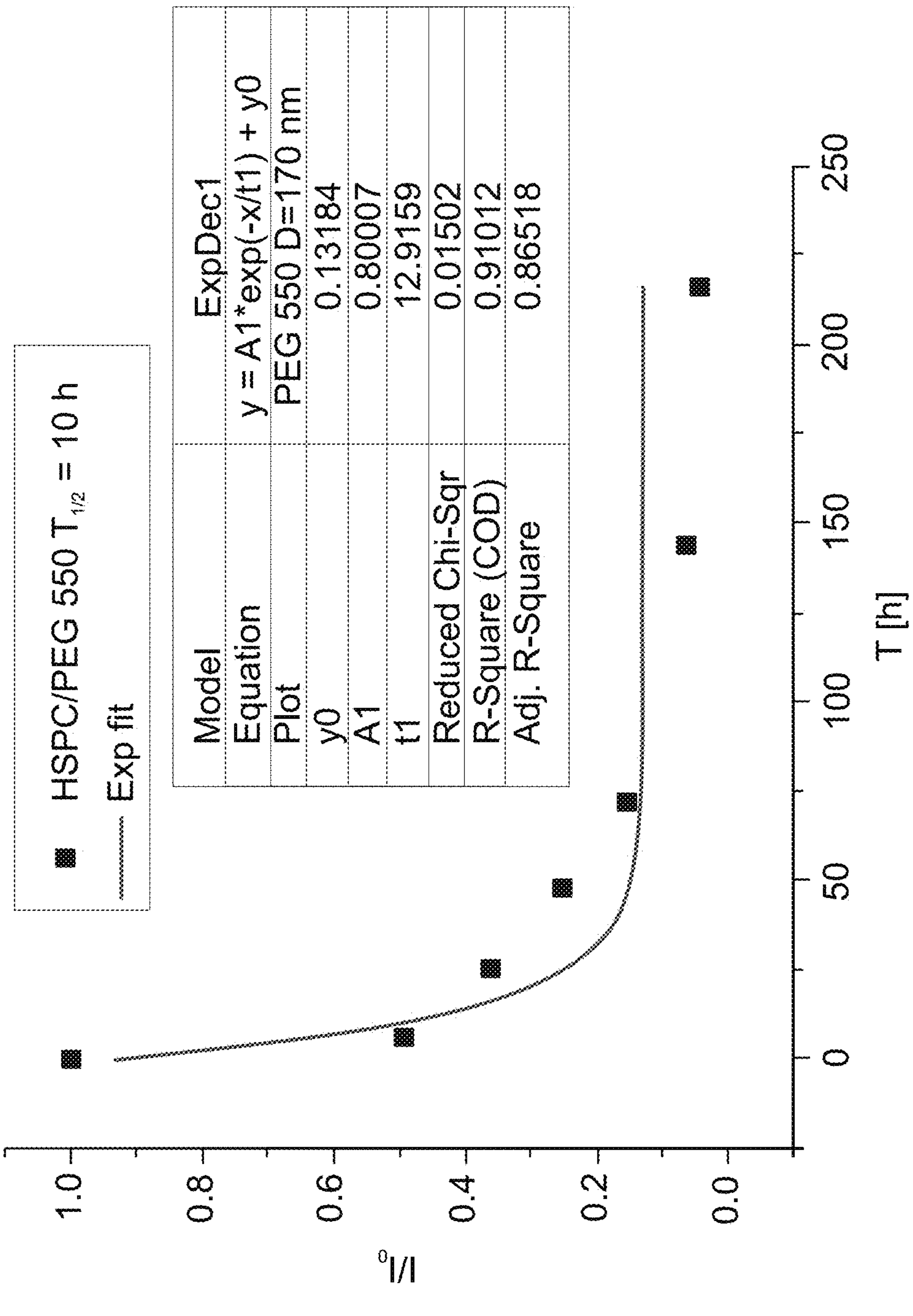
FIG. 5 presents a graph showing fluorescence signals in a mouse as a function of time after intra-articular injection of fluorescent-labeled hydrogenated soy phosphatidylcholine (HSPC) liposomes with 550 Da PEG moieties, along with exponential fit to the data (from which a calculated half-life of 10 hours was derived); mean liposome diameter was 170 nm.

As shown in FIG. 5, the half-life of the liposomes PEGylated with 550 Da PEG was about 10 hours, similar to the half-life obtained with liposomes PEGylated with 2000 Da PEG (see FIG. 2C).

These results indicate that considerable enhancement of in vivo retention of 170 nm liposomes by pMPC (in comparison to PEG) observed herein is not associated with degree of polymerization of pMPC vs.PEG.

Results presented in FIGS. 2A-2D and 5 are summarized in Table 1 below.

TABLE 1

Half-lives ($T_{1/2}$) of HSPC (hydrogenated soy phosphatidylcholine) liposome systems and hyaluronic acid (HA) following intra-articular injection upon intra-articular injection into mice knee joints

| Composition | Liposome diameter [nm] | $T_{1/2}$ [hours] |
|---|---|---|
| HSPC + 2% PEG (2000 Da) | 170 | 20-26 (by exponential fit) 12-20 (by visual estimate) |
| HSPC + 2% PEG (550 Da) | 170 | 10 |
| HSPC + 2% pMPC (2000 Da) | 170 | 85-95 |
| HSPC + 2% pMPC (2000 Da) + 2% TAP | 162 | 90 |
| HA ($M_w$ = 2500 kDa) | | <1 |

In addition, liposomes were modified by incorporating 1,2-stearoyl-3-trimethylammonium-propane (chloride salt), which comprises trimethylammonium-propane (TAP) groups that impart a positive charge to the liposome. Liposomes having a diameter of 162 nm were prepared using a 96:2:2 molar ratio of HSPC to pMPC to TAP, and their retention upon IA injection was evaluated as described hereinabove.

Figure 2D:
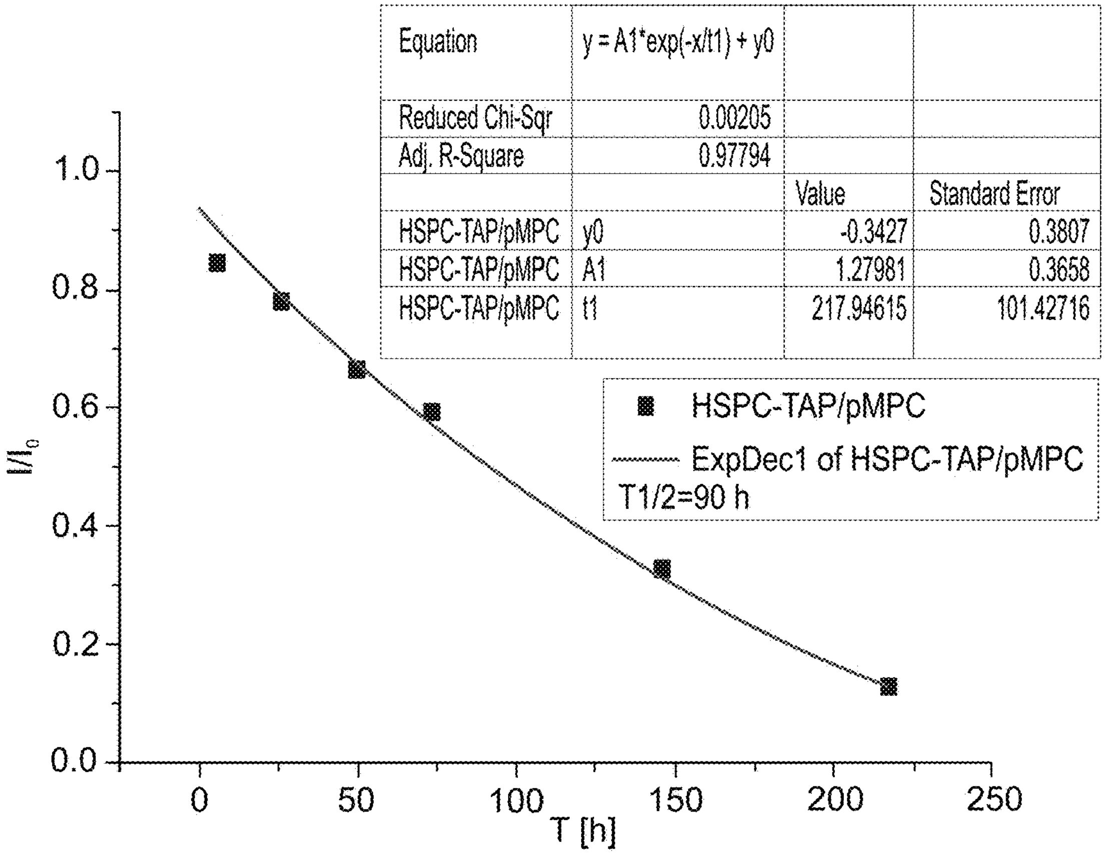

As shown in FIGS. 2A and 2D, liposomes comprising pMPC and TAP exhibited similar in vivo retention properties as did similarly sized liposomes comprising pMPC without TAP. It is noted that liposomes comprising HSPC and TAP without pMPC underwent aggregation after a few days.

Taken together, the above results indicate that pMPC-containing liposomes can be used to enhance retention of liposome-based drug-delivery vehicles, thereby improving sustained release of drugs, in comparison with state-of-the-art drug delivery using PEGylated liposomes.

Example 3

Retention of Additional Modified Liposomes Following Intra-Articular Injection Mice receive an intra-articular (IA) injection of modified liposomes, as described hereinabove, except that a targeting moiety (optionally a peptide) is attached to a pMPC moiety (optionally incorporated into a terminus of a DSPE-PMPC molecule as described hereinabove). The targeting moiety is selected to direct liposomes to a particular type of tissue. In some experiments, the peptide sequence WYRGRL (SEQ ID NO: 2) (a collagen-binding peptide) is attached to a pMPC moiety which facilitates direction of the liposomes to collagen-rich tissue (e.g., cartilage).

Retention (and optionally location) of the liposomes is monitored using a near infra-red camera and DiR fluorescent label, as described in Example 2.

In addition, mice are sacrificed at various time points (e.g., 1, 3, 7 and 14 days after injection), and histological cross-section samples are prepared from the mice knee joints. The precise location of injected liposomes in the tissue is investigated using a fluorescent microscope.

Example 4

Retention of Modified Liposomes Following Intravenous Administration

Subjects (optionally mice) receive an intravenous injection of modified liposomes, prepared as described hereinabove, except that rhodamine-phosphatidylethanolamine (Avanti Polar Lipids) is incorporated into liposomes (instead of DiR). Rhodamine fluorescence in blood of subjects is measured in order to evaluate liposome presence in the blood as a function of time following injection.

The results show considerable retention of the liposomes administered intravenously, indicating that the liposomes are suitable for sustained drug delivery via routes of administration other than intra-articular injection.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

It is the intent of the Applicant(s) that all publications, patents and patent applications referred to in this specification are to be incorporated in their entirety by reference into the specification, as if each individual publication, patent or patent application was specifically and individually noted when referenced that it is to be incorporated herein by reference. In addition, citation or identification of any reference in this application shall not be construed as an admission that such reference is available as prior art to the present invention. To the extent that section headings are used, they should not be construed as necessarily limiting. In addition, any priority document(s) of this application is/are hereby incorporated herein by reference in its/their entirety.

What is claimed is:

1. A method of treating a synovial joint disorder in a subject in need thereof, the method comprising administering to the subject a liposome comprising:

a) at least one bilayer-forming lipid;

b) a polymeric compound having the general formula I:

Formula I

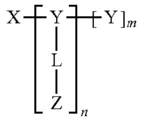

wherein:

m is zero or a positive integer;

n is an integer which is at least 3;

Y is a backbone unit which forms a polymeric backbone;

L is absent or is a linking moiety; and

Z has the general formula II:

Formula II

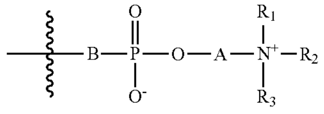

wherein:

A is a substituted or unsubstituted hydrocarbon;

B is an oxygen atom;

$R_1$-$R_3$ are each independently selected from the group consisting of hydrogen, alkyl, cycloalkyl, heteroalicyclic, aryl and heteroaryl; and

SEQUENCE LISTING

```
Sequence total quantity: 2
SEQ ID NO: 1           moltype = AA  length = 12
FEATURE                Location/Qualifiers
REGION                 1..12
                       note = a hyaluronic acid-binding peptide sequence
source                 1..12
                       mol_type = protein
                       organism = synthetic construct
SEQUENCE: 1
GAHWQFNALT VR                                                      12

SEQ ID NO: 2           moltype = AA  length = 6
FEATURE                Location/Qualifiers
REGION                 1..6
                       note = Examples of collagen-binding polypeptide
source                 1..6
                       mol_type = protein
                       organism = synthetic construct
SEQUENCE: 2
WYRGRL                                                             6
```

X is a lipid moiety having the general formula III:

Formula III

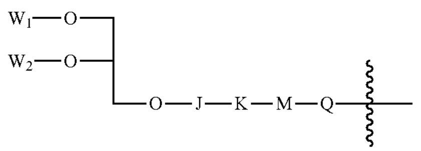

wherein:

$W_1$ and $W_2$ are each independently selected from the group consisting of hydrogen, alkyl, alkenyl, alkynyl and acyl, wherein at least one of $W_1$ and $W_2$ is not hydrogen;

J is —P(═O)(OH)—O— or absent;

K is a substituted or unsubstituted hydrocarbon from 1 to 10 carbon atoms in length, or absent;

M is a linking group selected from the group consisting of —O—, —S—, amino, sulfinyl, sulfonyl, phosphate, phosphonyl, phosphinyl, carbonyl, thiocarbonyl, urea, thiourea, carbamyl, thiocarbamyl, amido, carboxy, and sulfonamide, or absent; and Q is a substituted or unsubstituted hydrocarbon from 1 to 10 carbon atoms in length, wherein when M is absent, K is also absent; and c) a therapeutically active agent, incorporated in the liposome and/or on a surface of the liposome, said therapeutically active agent being selected from an analgesic, an anti-inflammatory agent, an anti-proliferative agent, an anti-microbial agent, and a vaccine antigen, thereby treating the synovial joint disorder.

2. The method according to claim 1, wherein said therapeutically active agent is selected from the group consisting of an analgesic, an anti-inflammatory agent and an anti-microbial agent.

3. The method according to claim 1, wherein said administering is by parenteral systemic administration.

4. The method according to claim 1, wherein administering is by intra-articular administration.

5. The method according to claim 1, wherein said synovial joint disorder is selected from the group consisting of arthritis, bursitis, carpal tunnel syndrome, fibromyositis, gout, locked joint, tendinitis, traumatic joint injury, and joint injury associated with surgery.

6. The method according to claim 1, wherein Y is a substituted or unsubstituted alkylene unit.

7. The method according to claim 6, wherein Y has the formula $—CR_4R_5—CR_6D$-, wherein:

when Y is a backbone unit which is not attached to said L or said Z, D is $R_7$; and when Y is a backbone unit which is attached to said L or said Z, D is a covalent bond or a linking group attaching Y to said L or said Z, said linking group being selected from the group consisting of —O—, —S—, alkylene, arylene, sulfinyl, sulfonyl, phosphate, phosphonyl, phosphinyl, carbonyl, thiocarbonyl, urea, thiourea, O-carbamyl, N-carbamyl, O-thiocarbamyl, N-thiocarbamyl, C-amido, N-amido, C-carboxy, O-carboxy, sulfonamido, and amino; and $R_4$-$R_7$ are each independently selected from the group consisting of hydrogen, alkyl, alkenyl, alkynyl, cycloalkyl, aryl, heteroaryl, heteroalicyclic, halo, hydroxy, alkoxy, aryloxy, thiohydroxy, thioalkoxy, thioaryloxy, sulfinyl, sulfonyl, cyano, nitro, azide, azo, phosphate, phosphonyl, phosphinyl, oxo, carbonyl, thiocarbonyl, urea, thiourea, O-carbamyl, N-carbamyl, O-thiocarbamyl, N-thiocarbamyl, C-amido, N-amido, C-carboxy, O-carboxy, sulfonamido, and amino.

8. The method according to claim 7, wherein said linking group is selected from the group consisting of —O—, —C(═O)O—, —C(═O)NH— and phenylene.

9. The method according to claim 7, wherein L is a substituted or unsubstituted hydrocarbon from 1 to 10 carbon atoms in length.

10. The method according to claim 1, wherein A is a substituted or unsubstituted hydrocarbon from 1 to 4 carbon atoms in length.

11. The method according to claim 1, wherein at least a portion of said Y, said L and/or said Z comprises at least one targeting moiety.

12. The method according to claim 1, wherein said lipid is selected from the group consisting of a fatty acid, a monoglyceride, a diglyceride, a triglyceride, a glycerophospholipid, a sphingolipid, and a sterol.

13. The method according to claim 1, wherein J is —P(═O)(OH)—O— and K is selected from the group consisting of an ethanolamine moiety, a serine moiety, a glycerol moiety and an inositol moiety.

14. The method according to claim 1, wherein M is amido.

15. The method according to claim 1, wherein J and K are absent and M is carbonyl.

16. The method according to claim 1, wherein Q is dimethylmethylene ($—C(CH_3)_2—$).

17. The method according to claim 1, wherein at least one of $W_1$ and $W_2$ is alkyl, alkenyl, alkynyl or acyl, being from 10 to 30 carbon atoms in length.

18. The method according to claim 1, wherein said lipid moiety comprises at least one fatty acid moiety selected from the group consisting of lauroyl, myristoyl, palmitoyl, stearoyl, palmitoleoyl, oleoyl, and linoleoyl.

19. The method according to claim 1, wherein said liposome is formulated as part of a pharmaceutical composition, which further comprises a pharmaceutically acceptable carrier.

20. The method according to claim 19, wherein said carrier comprises an aqueous liquid.

21. The method according to claim 19, wherein said pharmaceutical composition further comprises a water-soluble biopolymer.

* * * * *